(12) United States Patent
Ishizeki et al.

(10) Patent No.: US 8,360,056 B2
(45) Date of Patent: Jan. 29, 2013

(54) MEDICINE SPRAYER

(75) Inventors: Kazunori Ishizeki, Gunma (JP); Hisatomo Ohki, Isesaki (JP); Shigemi Nakamura, Isesaki (JP); Akira Yanagawa, Yokohama (JP)

(73) Assignees: Hitachi, Ltd., Tokyo (JP); Dott Limited Company, Kanagawa (JP)

( * ) Notice: Subject to any disclaimer, the term of this patent is extended or adjusted under 35 U.S.C. 154(b) by 968 days.

(21) Appl. No.: 12/310,521

(22) PCT Filed: Aug. 31, 2007

(86) PCT No.: PCT/JP2007/067036
§ 371 (c)(1),
(2), (4) Date: Feb. 27, 2009

(87) PCT Pub. No.: WO2008/026730
PCT Pub. Date: Mar. 6, 2008

(65) Prior Publication Data
US 2010/0175696 A1    Jul. 15, 2010

(30) Foreign Application Priority Data
Aug. 31, 2006  (JP) ................. 2006-236622

(51) Int. Cl.
*A61M 15/00*  (2006.01)
*A61M 16/00*  (2006.01)
*B05D 7/14*  (2006.01)
*B65D 83/06*  (2006.01)

(52) U.S. Cl. ..................... 128/203.21; 128/203.15

(58) Field of Classification Search . 128/200.14–200.24, 203.12, 203.14–204.23; 604/57–58, 244, 516
See application file for complete search history.

(56) References Cited

U.S. PATENT DOCUMENTS

| | | | | | |
|---|---|---|---|---|---|
| 5,899,202 | A | * | 5/1999 | Ohki et al. | 128/203.22 |
| 5,901,703 | A | * | 5/1999 | Ohki et al. | 128/203.12 |
| 5,921,236 | A | * | 7/1999 | Ohki et al. | 128/203.15 |
| 5,989,217 | A | * | 11/1999 | Ohki et al. | 604/94.01 |
| 6,543,443 | B1 | * | 4/2003 | Klimowicz et al. | 128/200.23 |
| 7,131,441 | B1 | * | 11/2006 | Keller et al. | 128/203.15 |
| 2004/0173211 | A1 | | 9/2004 | Kladders et al. | |

FOREIGN PATENT DOCUMENTS

| | | |
|---|---|---|
| JP | 58-041067 | 9/1983 |
| JP | 05-058349 | 8/1993 |
| JP | 09-154948 | 6/1997 |
| JP | 3273712 | 2/2002 |

* cited by examiner

*Primary Examiner* — Oren Ginsberg
(74) *Attorney, Agent, or Firm* — Antonelli, Terry, Stout & Kraus, LLP.

(57) ABSTRACT

A body section 2 is formed with a capsule insertion hole 6. A movable section 3 includes a capsule puncture needle 9 arranged to be moved into or out of the capsule insertion hole 6. The body section 2 and the movable section 3 are connected to be relatively pivoted at least between a posture in which the capsule insertion hole 6 is exposed, and a posture in which the capsule insertion hole 6 is hid by the body section 2. The body section 2 (a side wall 6e of a protrusion 6a) is arranged to restrict the advancing movement of the capsule puncture needle 9 in the state in which the body section 2 and the movable section 3 are in the posture in which the capsule insertion hole 6 is exposed.

10 Claims, 25 Drawing Sheets

(a)

(b)

(c)

(a)

(b)

(a)

(b)

(a)

(b)

(a)

(b)

(a)

(b)

MEDICINE SPRAYER

TECHNICAL FIELD

This invention relates to a medicine sprayer.

BACKGROUND ART

Conventionally, there are proposed various medicine sprayers. A patent document 1 discloses one example of the medicine sprayers.

The medicine sprayer of the above patent document 1 is arranged to form holes in the capsule by a capsule puncture needle, and to discharge a medicine received in the capsule by the air supplied by the pressure. In particular, a medicine spraying portion is screwed in a capsule holder holding a capsule. A capsule puncture needle supported in the medicine spraying portion to be moved in the advancing and returning directions is moved to form the punctures in the capsule.
Patent document 1: U.S. Pat. No. 3,273,712

SUMMARY OF THE INVENTION

However, in the medicine sprayer of the patent document 1, the capsule puncture needle held in the medicine spraying portion to be moved in the advancing and returning directions can be moved even in a state in which the medicine sprayer is not screwed in the capsule holder. In this state, if the capsule puncture needle is moved in the advancing and returning directions, the capsule puncture needle is exposed to the outside of the medicine spraying portion, and the dust and the dirt may be adhered to the capsule puncture needle. It is not preferred in the sanitary aspect and the safety aspect.

It is, therefore, an object of the present invention to provide a medicine sprayer devised to solve the above-mentioned problems, and to prevent a capsule puncture needle from being exposed to the outside of the sprayer.

In the present invention to attain the above-mentioned object, the medicine sprayer includes a first divided member formed with a capsule holding portion holding the capsule; a second divided member including the capsule puncture needle arranged to be moved into or out of the capsule holding portion; the first divided member and the second divided member being connected to be relatively moved at least between a posture in which the capsule holding portion is exposed, and a posture in which the capsule holding portion is hid by the second divided member, the first divided member being arranged to restrict the advancing movement of the capsule puncture needle when the first divided member and the second divided member are in the posture in which the capsule holding portion is exposed. This feature is a first feature according to the present invention. Moreover, the present invention may include second to fourteenth features.

In the second feature according to the present invention, the first divided member includes a capsule insertion hole serving as the capsule holding portion; the first divided member and the second divided member are connected to be relatively pivoted at least between a posture in which the capsule insertion hole is exposed, and a posture in which the capsule insertion hole is hid; an outlet of the capsule puncture needle from the second divided member confronts an opening portion of the capsule insertion hole when the first divided member and the second divided member are in the posture in which the capsule insertion hole is hid so that the capsule puncture needle is arranged to be moved from the opening portion into the capsule insertion hole; and the outlet confronts an outer side of a side wall when the first divided member and the second divided member are in the posture in which the capsule insertion hole is exposed so that the side wall restricts the advancing movement of the capsule puncture needle.

In the third feature according to the present invention, the first divided member includes a cylindrical protrusion; the capsule insertion hole is a cylindrical hole of the protrusion; the second divided member includes a pair of arm portions arranged to sandwich the protrusion; one of the protrusion and the arm portions includes a guide groove; the other of the protrusion and the arm portions includes a guide groove arranged to be guided in the guide groove; an end surface of the protrusion and a bottom surface between the pair of the arm portions are abutted on each other when the first divided member and the second divided member are in the posture in which the capsule insertion hole is hid so that the bottom surface closes the opening portion of the capsule insertion hole; the guide groove includes a portion extending in a direction in which the end surface and the bottom surface is abutted on or separated from each other so that the end surface and the bottom surface are separated from each other when the first divided member and the second divided member are changed from the posture in which the capsule insertion hole is hid to the posture in which the capsule insertion hole is exposed.

In the fourth feature according to the present invention, the first divided member includes a capsule insertion hole serving as the capsule holding portion; the first divided member and the second divided member are connected to be relatively slid at least between a posture in which the capsule insertion hole is exposed, and a posture in which the capsule insertion hole is hid; an outlet of the capsule puncture needle from the second divided member confronts an opening portion of the capsule insertion hole when the first divided member and the second divided member are in the posture in which the capsule insertion hole is hid so that the capsule puncture needle is moved from the opening portion into the capsule insertion hole; and the outlet confronts an upper wall of the capsule insertion hole when the first divided member and the second divided member are in the posture in which the capsule insertion hole is exposed so that the upper wall restricts the advance movement of the capsule puncture needle.

In the fifth feature according to the present invention, the first divided member includes a cylindrical protrusion; the capsule insertion hole is a cylindrical hole of the protrusion; the second divided member includes a pair of arm portions arranged to sandwich the protrusion; one of protrusion and the arm portion includes a guide groove; the other of the protrusion and the arm portions includes a guide portion arranged to be guided in the guide groove; an end surface of the protrusion and the bottom surface between the pair of the arm portions are abutted on each other when the first divided member and the second divided member are in the posture in which the capsule insertion hole is hid so that the bottom surface closes an opening portion of the capsule insertion hole; the protrusion includes a portion extending in a direction in which the opening portion of the capsule insertion hole and the outlet of the capsule puncture needle are deviated from each other so that the opening portion and the outlet are separated form each other when the first divided member and the second divided member are changed from the posture in which the capsule insertion hole is hid to the posture in which the capsule insertion hole is exposed.

In the sixth feature according to the present invention, the first divided member include a capsule insertion hole serving as the capsule holding portion; the first divided member and the second divided member are connected to be relatively inclined at least between a posture in which the capsule insertion hole is exposed, and a posture in which the capsule insertion hole is hid; an outlet of the capsule puncture needle from the second divided member confronts an opening portion of the capsule insertion hole when the first divided member and the second divided member are in the posture in which the capsule insertion hole is hid so that the capsule puncture needle is arranged to be moved from the opening portion into the capsule insertion hole; and the outlet confronts an outer side of a side wall of the capsule insertion hole when the first divided member and the second divided member are in the posture in which the capsule insertion hole is exposed so that the side wall restricts the advance movement of the capsule puncture needle.

In the seventh feature according to the present invention, the first divided member includes a capsule insertion hole serving as the capsule holding portion; the first divided member and the second divided member are connected to be relatively inclined at least between a posture in which the capsule insertion hole is exposed, and a posture in which the capsule insertion hole is hid; an outlet of the capsule puncture needle from the second divided member confronts an opening portion of the capsule insertion hole when the first divided member and the second divided member are in the posture in which the capsule insertion hole is hid so that the capsule puncture needle is arranged to be moved from the opening portion into the capsule insertion hole; the second divided member includes a covering portion arranged to cover the capsule holding portion, and to be moved at a stage before the relative inclination of the first divided member and the second divided member; and the covering portion is arranged to restrict the advance of the capsule puncture needle at the stage before the relative inclination of the first divided member and the second divided member.

In the eighth feature according to the present invention, the covering portion includes a puncture hole arranged to pass the capsule puncture needle to the capsule insertion hole in the posture in which the capsule insertion hole is hid by the second divided member.

In the ninth feature according to the present invention, the guide groove includes a portion extending substantially in a direction crossing a direction in which the end surface and the bottom surface are abutted on or separated from each other.

In the tenth feature according to the present invention, the protrusion is formed into a cylindrical shape; the guide groove and the guide member are provided in a symmetrical manner with respect to a central axis of the protrusion; the guide member is mounted in the guide groove to serve as a pivot axis of the relative pivot of the first divided member and the second divided member.

In the eleventh feature according to the present invention, the capsule puncture needle is arranged to pass through the capsule held in the capsule insertion hole; a medicine receiving chamber is formed at an end portion of the capsule puncture needle passing through the capsule; the air passage is arranged to introduce the air supplied by the pressure from the air pump mechanism, into the medicine receiving chamber; and the air passage extends in a direction crossing a discharge direction of the medicine and the air from the medicine receiving chamber.

In the twelfth feature according to the present invention, the capsule holding portion includes a bottom surface formed into a substantially semiround shape which is substantially closely attached to an end portion of the capsule.

In the thirteenth feature according to the present invention, the medicine receiving chamber is formed into a substantially cylindrical shape extending along an outer shape of the capsule; and the medicine receiving chamber includes a plurality of air passages connected in a tangent direction of an inner cylindrical surface, and arranged in a substantially winding shape.

In the fourteenth feature according to the present invention, the medicine sprayer further comprises an outer skin section arranged to closely attached to an end portion formed with a discharge hole of the medicine, and to be detachable.

BRIEF DESCRIPTION OF DRAWINGS

FIG. 21(a) is a plan view. FIG. 21(b) is a front view.

FIG. 22(a) is a plan view. FIG. 22(b) is a front view.

FIG. 23(a) is a plan view. FIG. 23(b) is a front view.

FIG. 24(a) is a sectional view taken along a line A-A of FIG. 24(b). FIG. 24(b) is a side view.

FIG. 25(a) is a sectional view taken along a line B-B of FIG. 25(b).

DETAILED DESCRIPTION OF THE INVENTION

Figure 1:
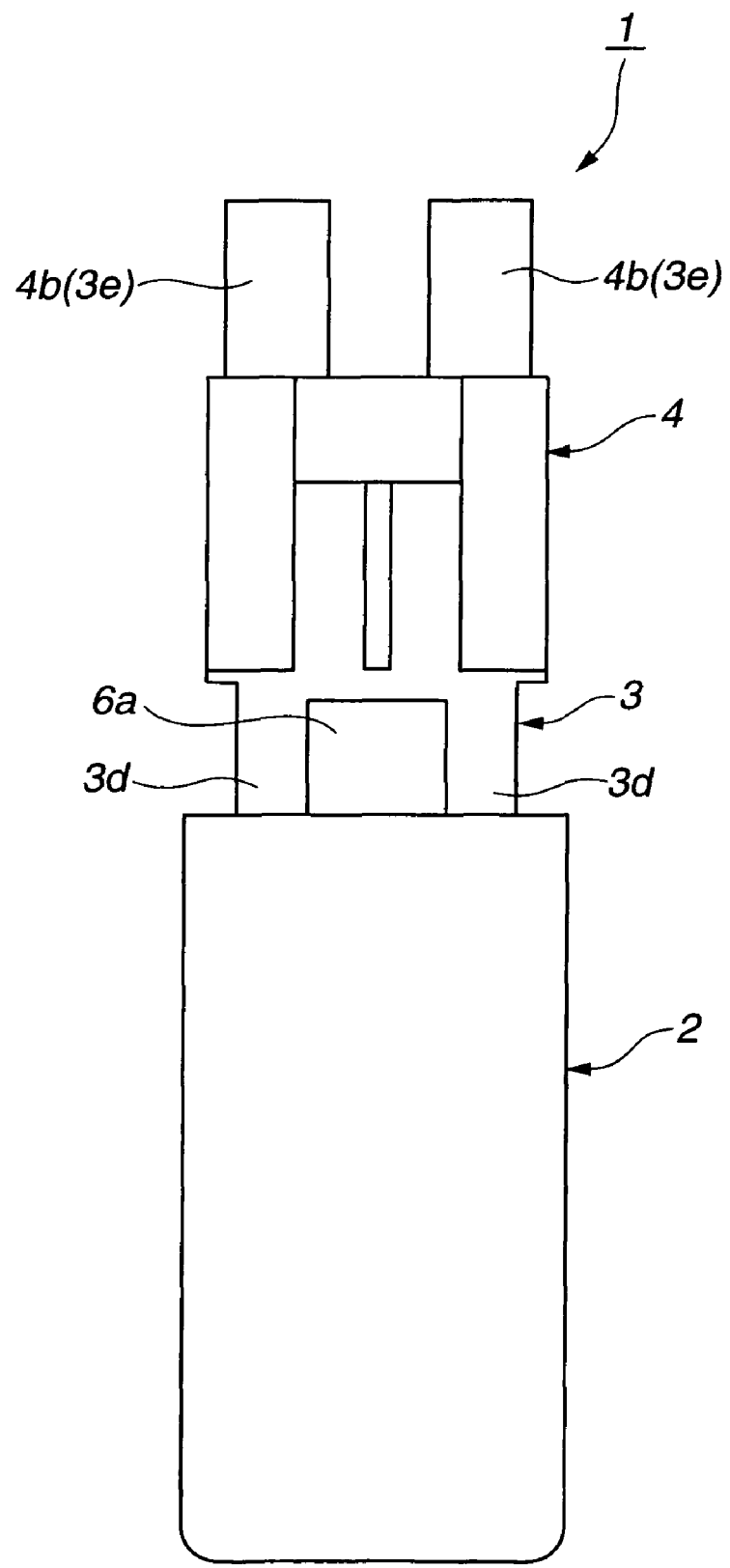
FIG. 1 is a front view showing an appearance of a medicine sprayer according to a first embodiment of the present invention.

By a first feature of the present invention, the second divided member holding the capsule puncture needle is not separated from the first divided member, and the first divided member is arranged to restrict the advance movement of the capsule puncture needle when the capsule holding portion is exposed to attach or detach the capsule. Accordingly, it is possible to ensure the sanitary and the safety without touching the capsule puncture needle.

By a second feature of the present invention, the outlet of the capsule puncture needle confronts the outer surface of the side wall of the capsule insertion hole when the first divided member and the second divided member are in the posture in which the capsule insertion hole is exposed. Accordingly, it is possible to exemplify the structure in which the first divided member is arranged to restrict the advance movement of the capsule puncture needle, by the further simple structure.

By a third feature of the present invention, in a state in which the guide member is guided by the guide groove, the end surface of the protrusion and the bottom surface between the pair of the arm portions are abutted on each other to ensure the sealing characteristic at this portion. In the state in which the guide member is guided by the portion extending in a direction in which the end surface and the bottom surface of the guide groove are abutted on or separated from each other, the end surface and the bottom surface are separated from each other. Accordingly, it is possible to further readily relatively pivot the first divided member and the second divided member.

By a fourth feature of the present invention, the first divided member and the second divided member are connected with each other to be relatively slid. The outlet of the capsule puncture needle confronts the upper wall of the capsule insertion hole when the first divided member and the second divided member are in the posture in which the capsule insertion hole is exposed. Accordingly, it is possible to exemplify the structure in which the first divided member is arranged to restrict the advance movement of the capsule puncture needle in connection with the relative sliding movement of the first divided member and the second divided member, by the further simple structure.

By a fifth feature of the present invention, in a state in which the guide member is guided in the guide groove, the end surface of the protrusion and the bottom surface between the pair of the arm portions are abutted on each other to ensure the sealing characteristic at this portion. In the state in which the guide member is guided by the portion extending in a direction in which the end surface of the guide groove and the bottom are deviated from each other, the end surface and the bottom surface are separated from each other. Accordingly, it is possible to further readily relatively slide the first divided member and the second divided member.

By a sixth feature of the present invention, the first divided member and the second divided member are connected to be relatively inclined. The outlet of the capsule puncture needle confronts the outside of the side wall of the capsule insertion hole when the first divided member and the second divided member are in the inclined posture in which the capsule insertion hole is exposed. Accordingly, it is possible to exemplify the structure in which the first divided member is arranged to restrict the advance movement of the capsule puncture needle in connection with the relative inclination of the first divided member and the second divided member, by the further simple structure.

By a seventh feature of the present invention, in the stage before the relative inclination of the first divided member and the second divided member, the covering portion is arranged to restrict the advance movement of the capsule puncture needle. Accordingly, it is possible to restrict the advance movement of the capsule puncture needle, and to smoothly perform the relative inclination of the first divided member and the second divided member.

By an eighth feature, in the posture in which the capsule insertion hole is hid by the second divided member, it is possible to pass the capsule puncture needle through the puncture hole provided to the covering portion, to the capsule insertion hole.

By a ninth feature, the guide groove includes a portion extending substantially in a direction crossing a direction in which the end surface and the bottom surface are abutted on or separated from each other, so that the first divided member and the second divided member are engaged on each other in a direction in which the first divided member and the second divided member are abutted on or separated from each other. Accordingly, it is possible to suppress the first divided member and the second divided member from being separating from each other.

By a tenth feature, the protrusion is formed into the cylindrical shape, so that the guide mechanism and the relative pivot mechanism are commonly used. Accordingly, it is possible to simplify the structure. It has the axially symmetrical structure with respect to the central axis of the protrusion. Accordingly, it is possible to stabilize the postures at the relative movement by the guide mechanism and at the relative pivot movement by the relative pivot mechanism, and to obtain further certain operation.

By an eleventh feature of the present invention, it is possible to suppress the medicine spilled out from the puncture formed in the capsule by the medicine receiving chamber, from reversing to the air pump mechanism. The supplying direction and the discharging direction of the air within the medicine receiving chamber are crossed so as to promote the turbulence and the flow separation of the air flow, and to promote the stir of the air and the medicine. Accordingly, it is possible to discharge the medicine with the air, and to feed the medicine farther. Moreover, it is possible to suppress the medicine from remaining in the medicine sprayer.

By a twelfth feature of the present invention, it is possible to improve the contact between the capsule holding portion and the outer surface of the capsule, and to improve the sealing of the medicine.

By a thirteenth feature of the present invention, the swirl flow of the air is formed in the medicine receiving chamber, and it is possible to further promote the stir of the air and the medicine.

By a fourteenth feature of the present invention, the outer skin section is detachable, and it is possible to further readily keep the outer surface of the medicine sprayer in the clean state.

Hereinafter, a first embodiment embodying the present invention will be illustrated with reference to the drawings.

First Embodiment

Figure 2:
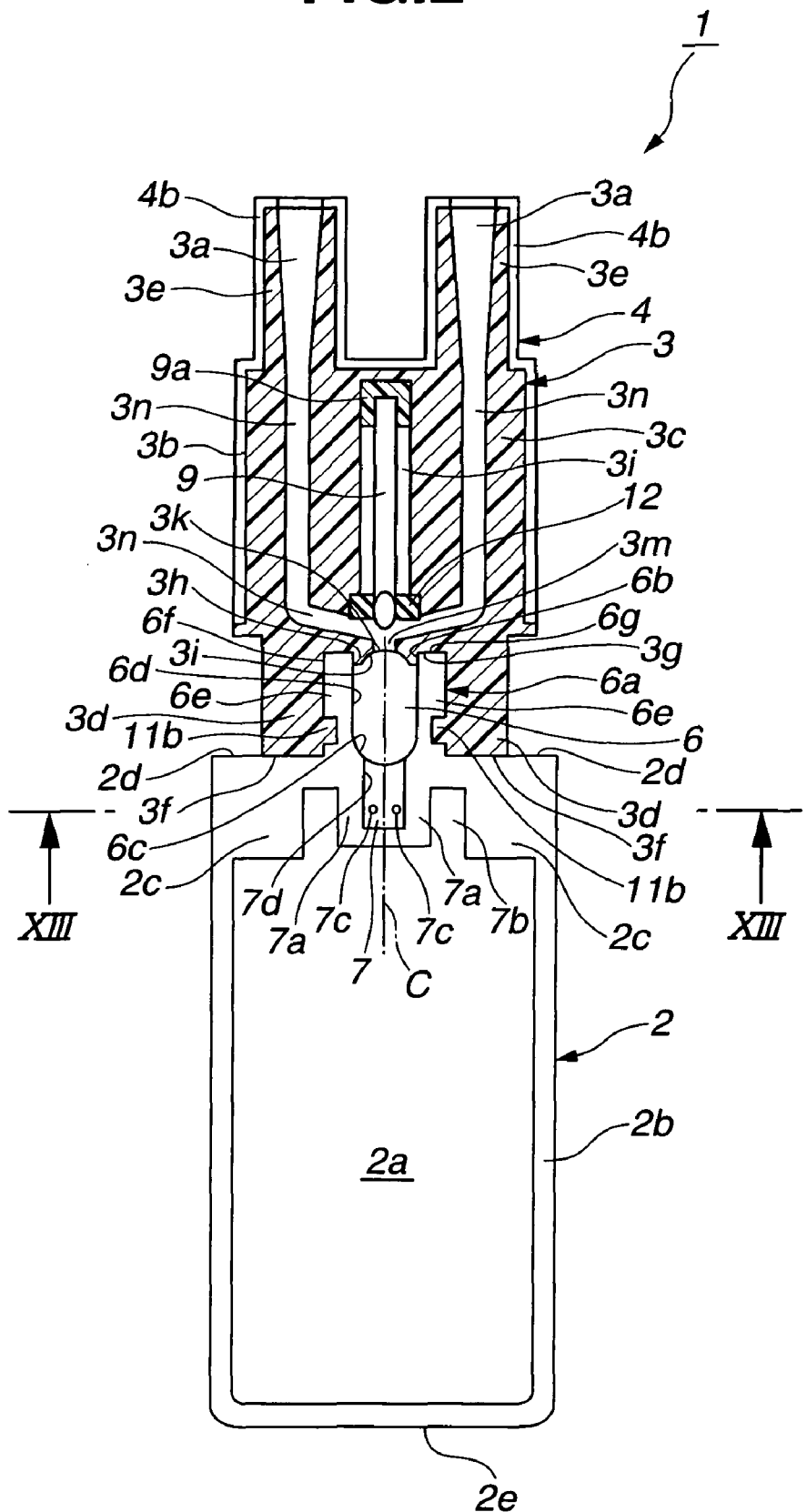
FIG. 2 is a longitudinal sectional view of the medicine sprayer according to the first embodiment of the present invention.
Figure 3:
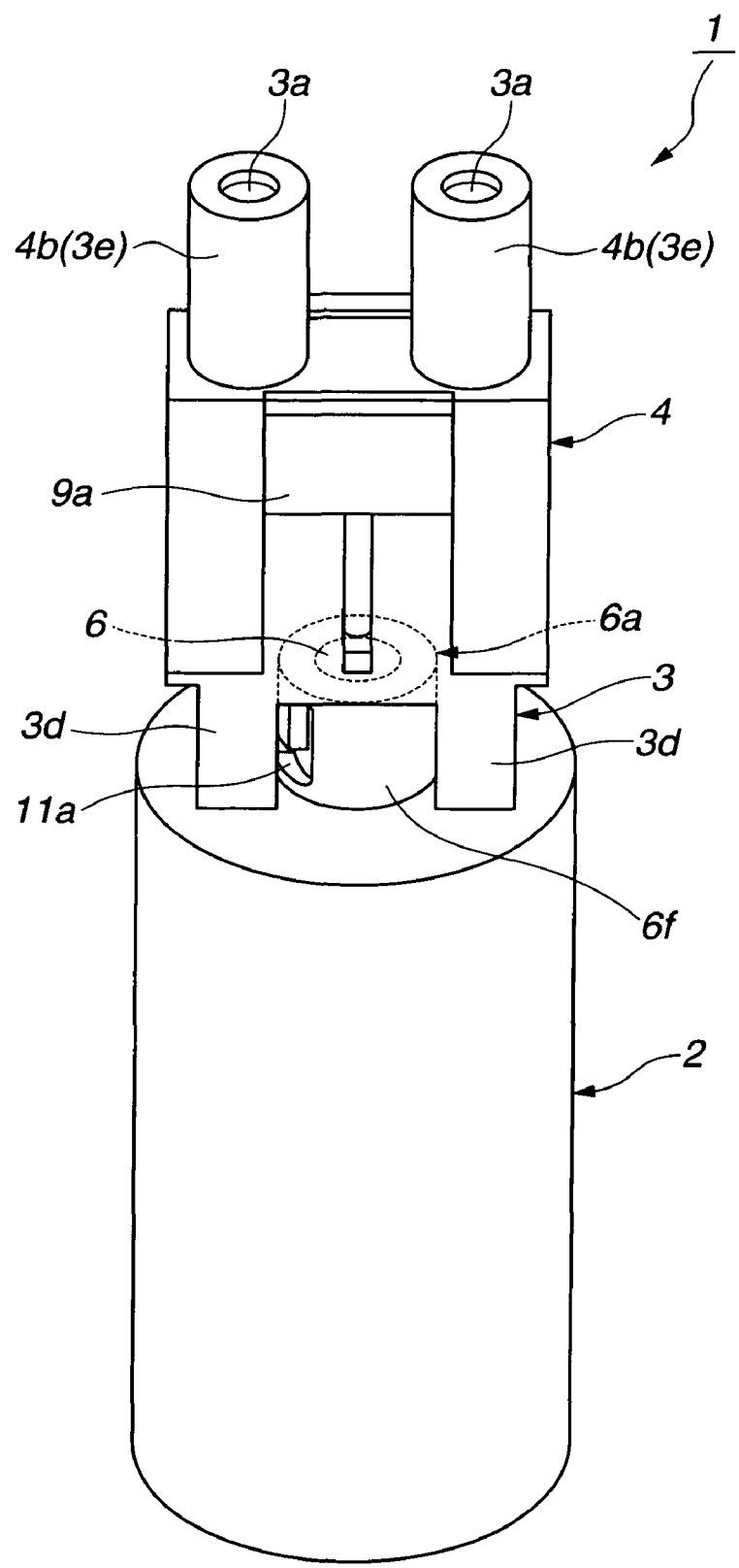
FIG. 3 is a perspective view of the medicine sprayer according to the first embodiment of the present invention.
Figure 4:
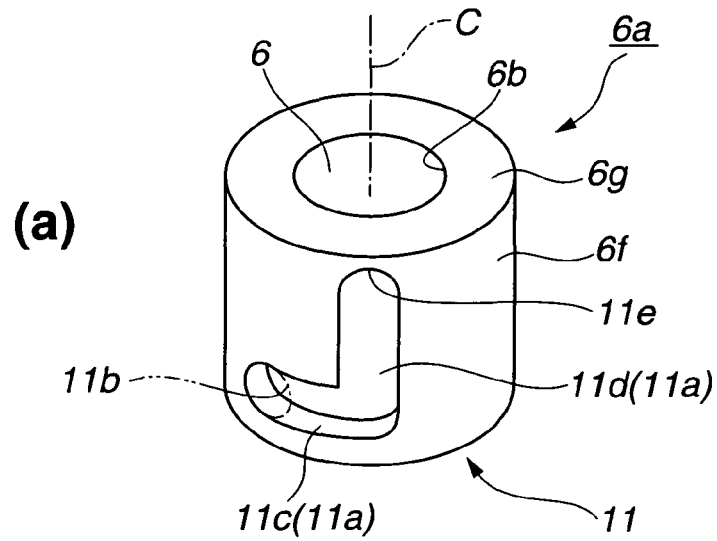
FIGS. 4(a)-(c) are a perspective view of a protrusion which forms a guide mechanism provided to the medicine sprayer.
Figure 4:
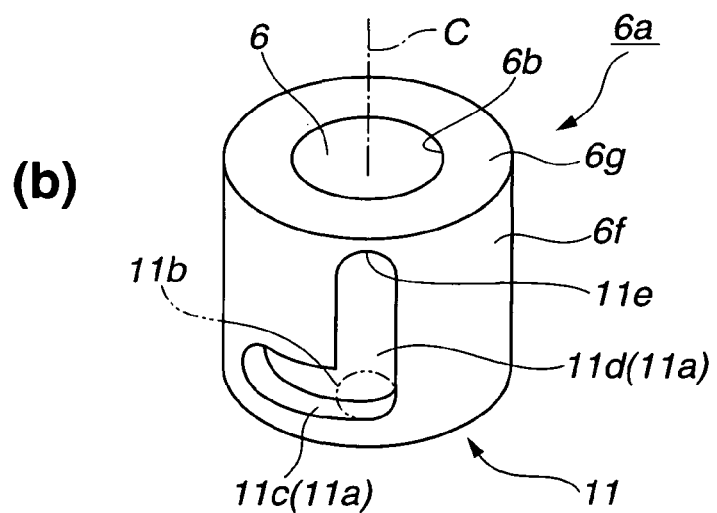
Figure 4:
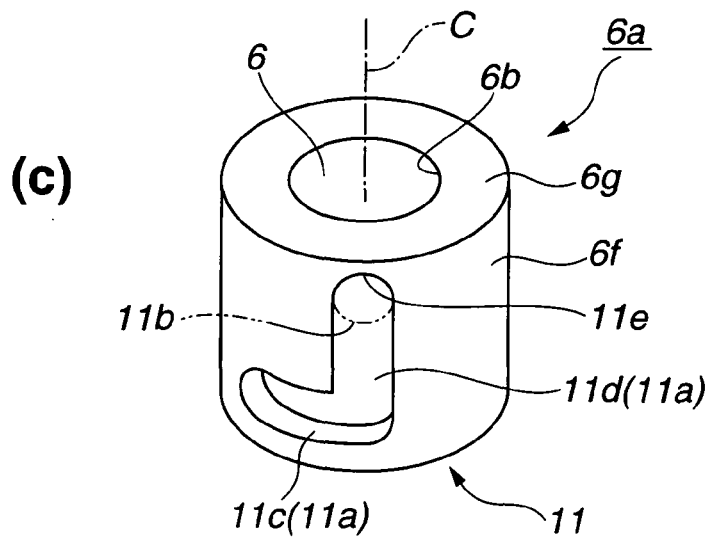
Figure 10:
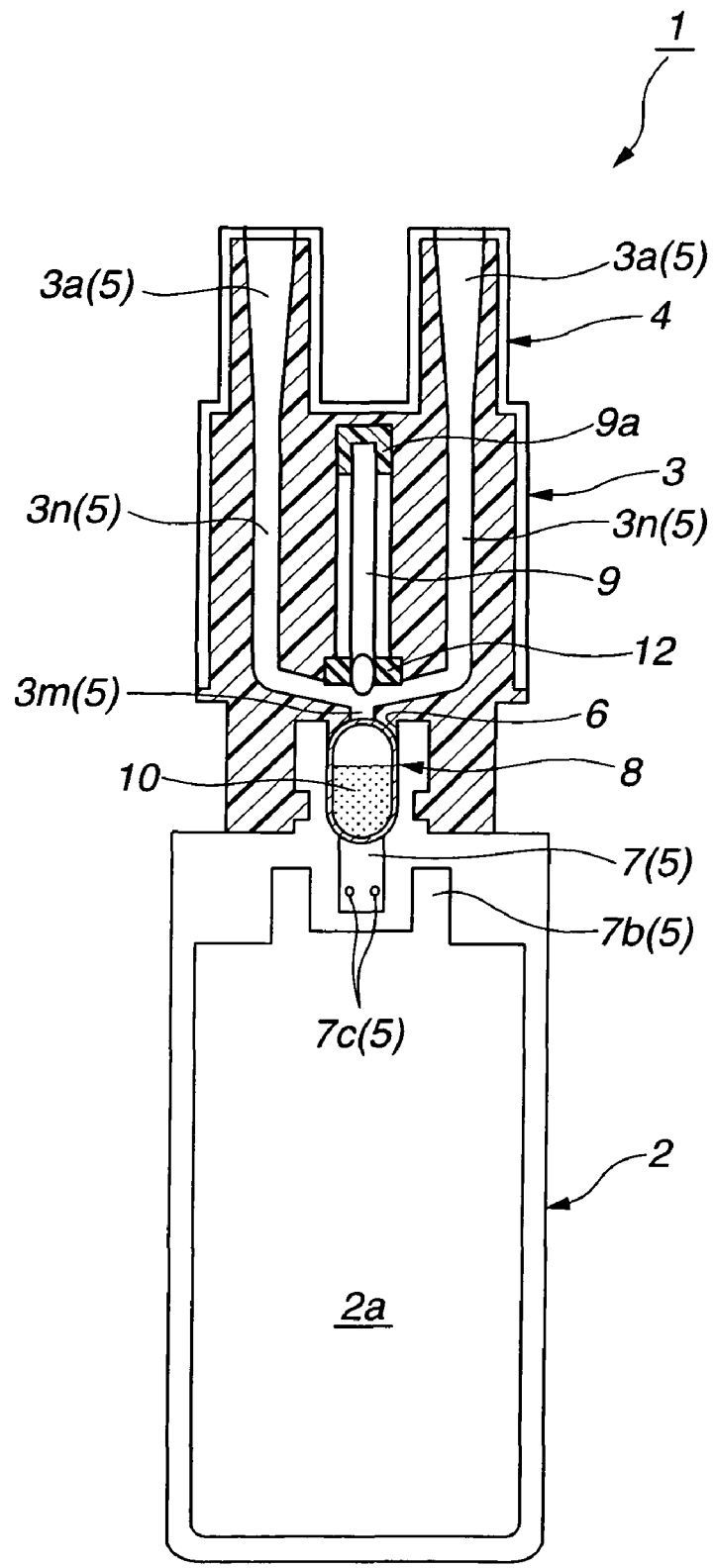
FIG. 10 is a longitudinal sectional view of the medicine sprayer according to the first embodiment of the present invention, and showing a state before a capsule puncture needle pierces a capsule inserted into a capsule insertion hole.
Figure 11:
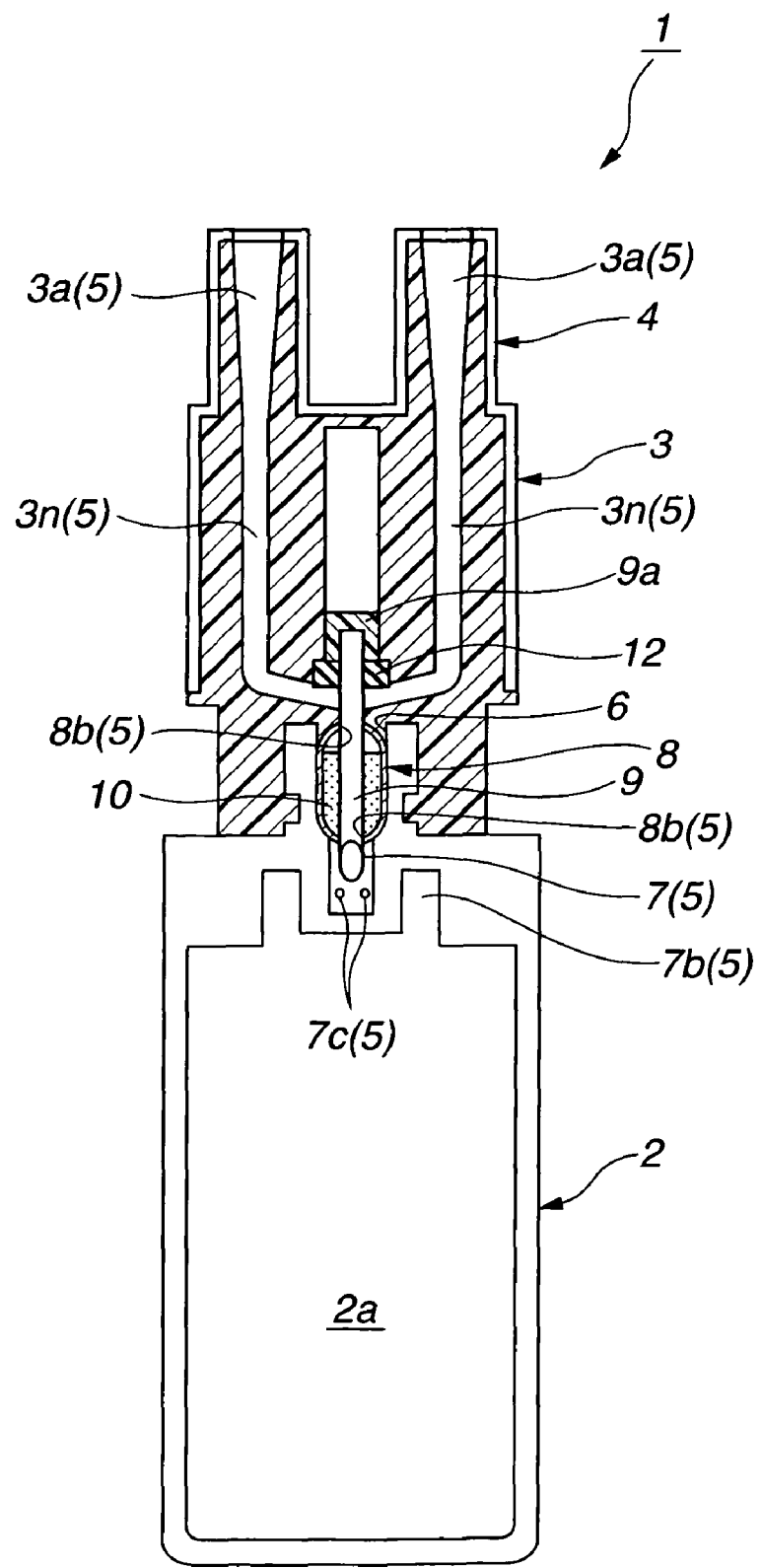
FIG. 11 is a longitudinal sectional view showing the medicine sprayer according to the first embodiment of the present invention, and showing a state in which the capsule puncture needle pierces the capsule.
Figure 12:
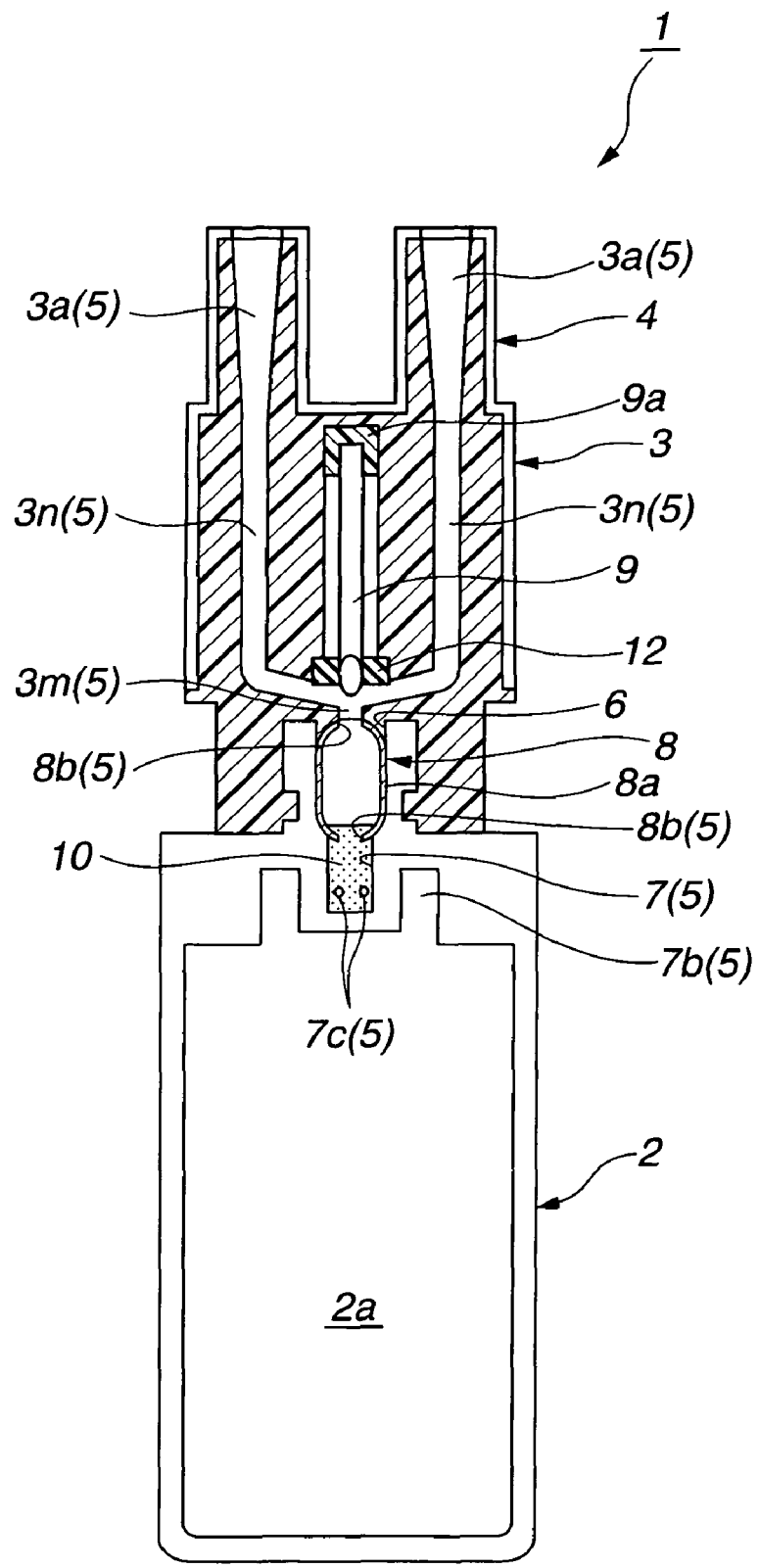
FIG. 12 is a longitudinal sectional view showing the medicine sprayer according to the first embodiment of the present invention, and showing a state in which the capsule puncture needle is returned to a needle receiving portion after the capsule puncture needle pierces to the capsule.
Figure 13:
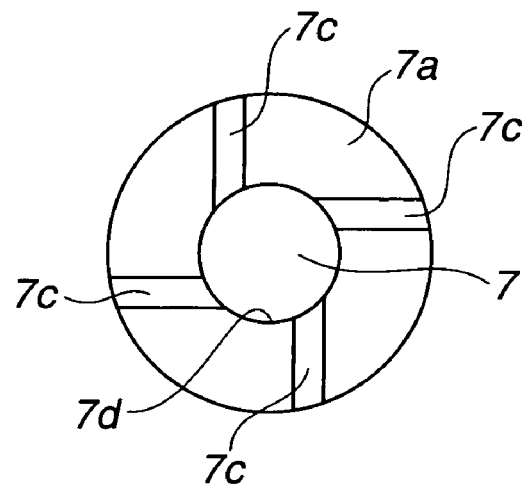
FIG. 13 is a sectional view taken along a line XIII-XIII of FIG. 2.
Figure 14:
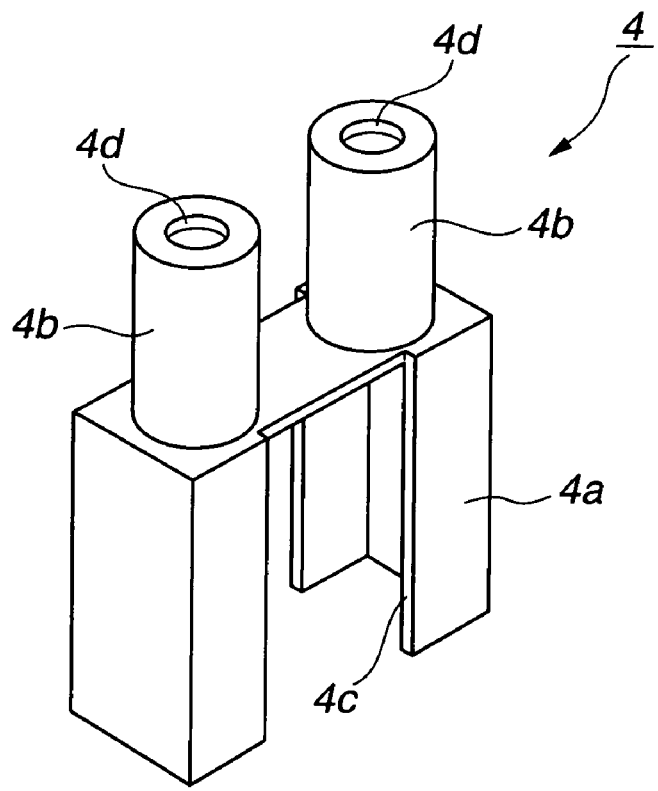
FIG. 14 is an outer skin section of the medicine sprayer according to the first embodiment of the present invention.

FIG. 1 is a front view showing an appearance of a medicine sprayer according to this embodiment. FIG. 2 is a longitudinal sectional view showing the medicine sprayer. FIG. 3 is a perspective view of the medicine sprayer. FIG. 4 is a perspective view of a protrusion provided to the medicine sprayer. FIGS. 5-8 are perspective views showing the medicine sprayer, and showing steps of relative movements of a first divided member and a second divided member. FIGS. 10-12 are longitudinal sectional views of the medicine sprayer, showing steps after holes are formed in a capsule held in a capsule holding portion, until the medicine within the capsule is discharged. FIG. 13 is a sectional view taken along a line XII-XII of FIG. 2. FIG. 14 is a perspective view showing an outer skin section detachably mounted on the medicine discharge port's side.

In this embodiment, the medicine sprayer 1 is applied to a powder medicine administering apparatus for administering a powder medicine into the nasal cavity.

The medicine sprayer 1 according to this embodiment includes a body section 2 serving as a first divided member; a movable section 3 serving as a second divided member connected to move relatively (pivot relatively) with respect to the body section 2; and an outer skin section 4 arranged to cover an outer surface 3b on the discharge hole 3a's side of the movable section 3.

The medicine sprayer 1 still stands by striking the bottomed portion 2e of the body section 2 on a plane such as a table. Hereinafter, an upward direction and a downward direction are defined with reference to this still standing posture (FIG. 1).

The body section 2 is formed by molding an elastomer with the flexibility into a case shape. The body section 2 includes an air chamber 2a formed within the body section 2. The air chamber 2a is contracted by pressing the outer wall 2b of the air chamber 2a by fingers and so on, so that the air within the air chamber 2a is discharged through air passages 5 (FIG. 10). That is, in this embodiment, the body section 2 serves as an air pump mechanism.

An end portion (upper portion) of the body section 2 on the movable section 3's side is a rigid portion 2c (FIG. 2) which does not vary largely by the press of the fingers and so on. Within the rigid portion 2c, there are formed a capsule insertion hole 6 serving as a capsule holding portion, and a medicine receiving chamber 7.

Figure 7:
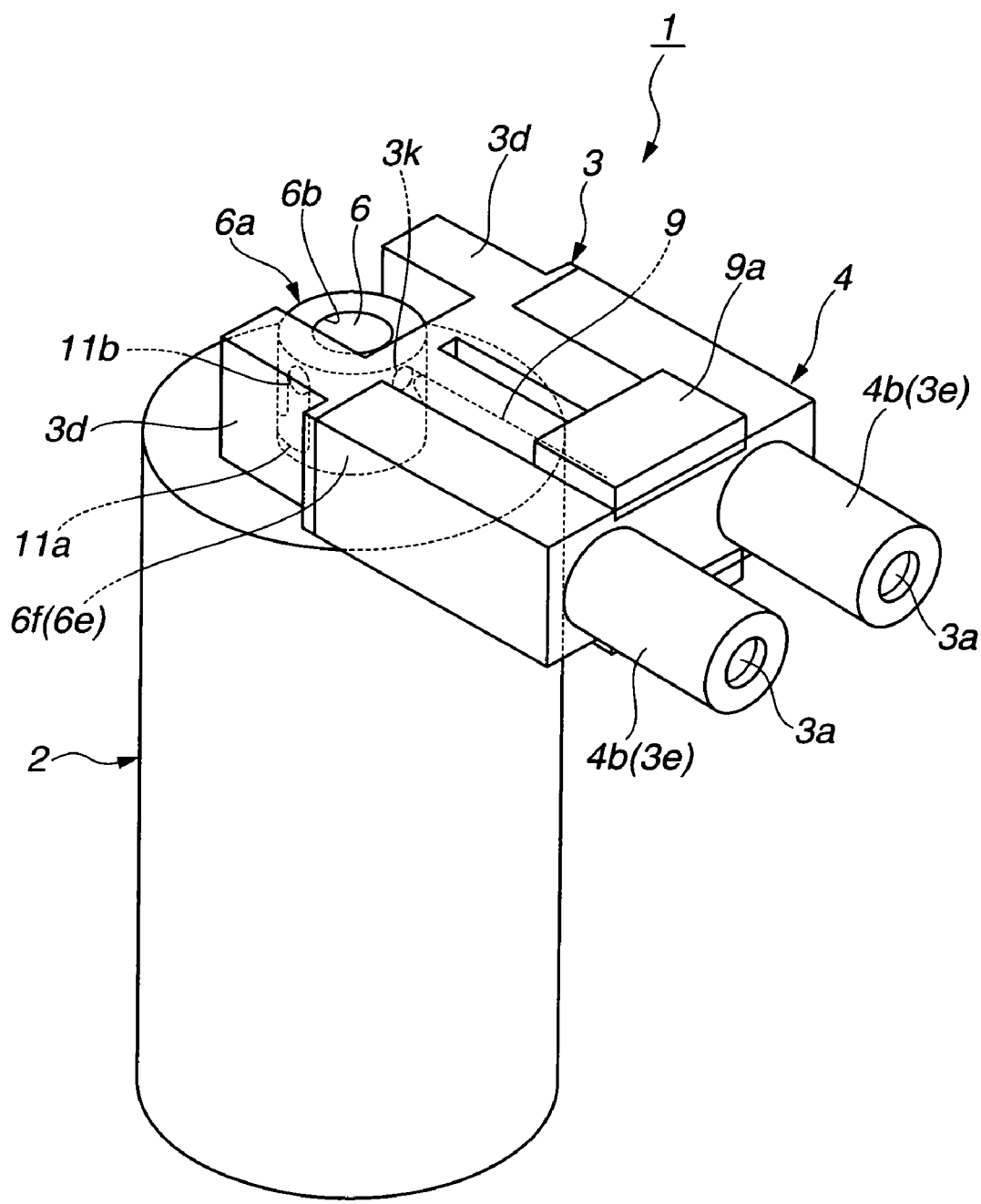
FIG. 7 is a perspective view of the medicine sprayer according to the first embodiment of the present invention, in which the second divided member is inclined by a substantially right angle with respect to the first divided member.
Figure 8:
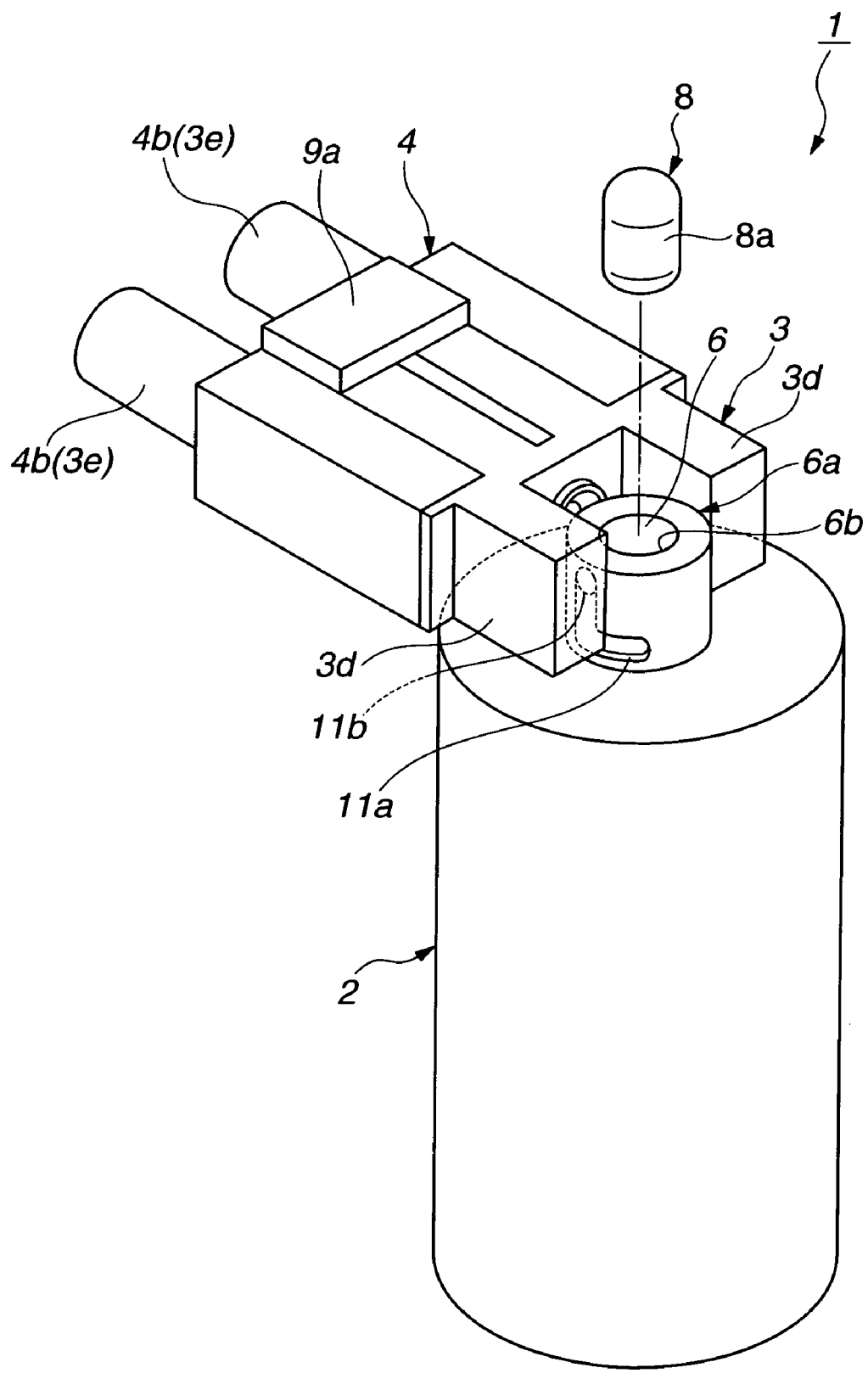
FIG. 8 is a perspective view of the medicine sprayer according to the first embodiment of the present invention, in which the second divided member is inclined by a substantially right angle with respect to the first divided member, and which is shown from the opposite side of FIG. 7.

The capsule insertion hole 6 is an inside of a cylindrical protrusion 6a protruding on an end surface 2d on the movable section 3's side. A capsule 8 can be inserted through an opening portion 6b into the capsule insertion hole in a state in which the movable section 3 is inclined to open the opening portion 6b (in a state in which the capsule insertion hole 6 is exposed: FIGS. 7, 8 and 9(c); as described later). As shown in FIG. 2, a bottomed portion 6c of the capsule insertion hole 6 is a spherical shape which substantially closely contacts a semiround portion of the capsule 8. An inner circumference surface 6d of the capsule insertion hole 6 is formed so as to guide a cylindrical portion of the capsule 8 at the insertion.

The medicine receiving chamber 7 (FIGS. 2 and 13) is a cylindrical space connected on the bottomed surface 6c's side of the capsule insertion hole 6. As shown in FIG. 12, the medicine receiving chamber 7 receives medicine 10 spilled (overflowed) from the capsule 8 through punctures 8b formed in the capsule 8 by a capsule puncture needle 9, so as to suppress the medicine 10 from entering into the air chamber 2a.

The medicine receiving chamber 7 is connected with the air chamber 2a through an annular groove portion 7b which is formed on the outer circumference of a side wall 7a, and side holes 7c which penetrate through the side wall 7a, and which is connected with the annular groove portion 7b. The air supplied by the pressure by the compression of the air chamber 2a is introduced though the annular groove portion 7b and the side holes 7c into the medicine receiving chamber 7. In this case, as shown in FIG. 13, the side holes 7c are opened in a plurality of portions (four portions at 90° in this example) appropriately arranged on an inner circumference surface 7d of the medicine receiving chamber 7 in the circumferential direction. Each of the side holes 7c extends along a tangent line at each opening portion in a substantially winding (vortical) manner. The air introduced from the side holes 7c into the medicine receiving chamber 7 forms rotational flow (vortex flow) in the medicine receiving chamber 7, so as to promote the stirring of the medicine 10 and the air. That is, in this embodiment, the medicine receiving chamber 7 serves as a stirred flow forming section arranged to form the stirred flow of the air supplied by the pressure and the medicine 10.

The movable section 3 (FIG. 2) includes a rigid portion 3c having a substantially rectangular cylindrical shape; a pair of arm portions 3d and 3d arranged to extend from the rigid portion 3c toward the body section 2, and to sandwich the protrusion 6a; and insertion portions 3e and 3e located on the opposite side of the arm portions 3d and 3d, and arranged to protrude from the rigid portion 3c, and to be inserted into the nasal cavity.

Figure 9:
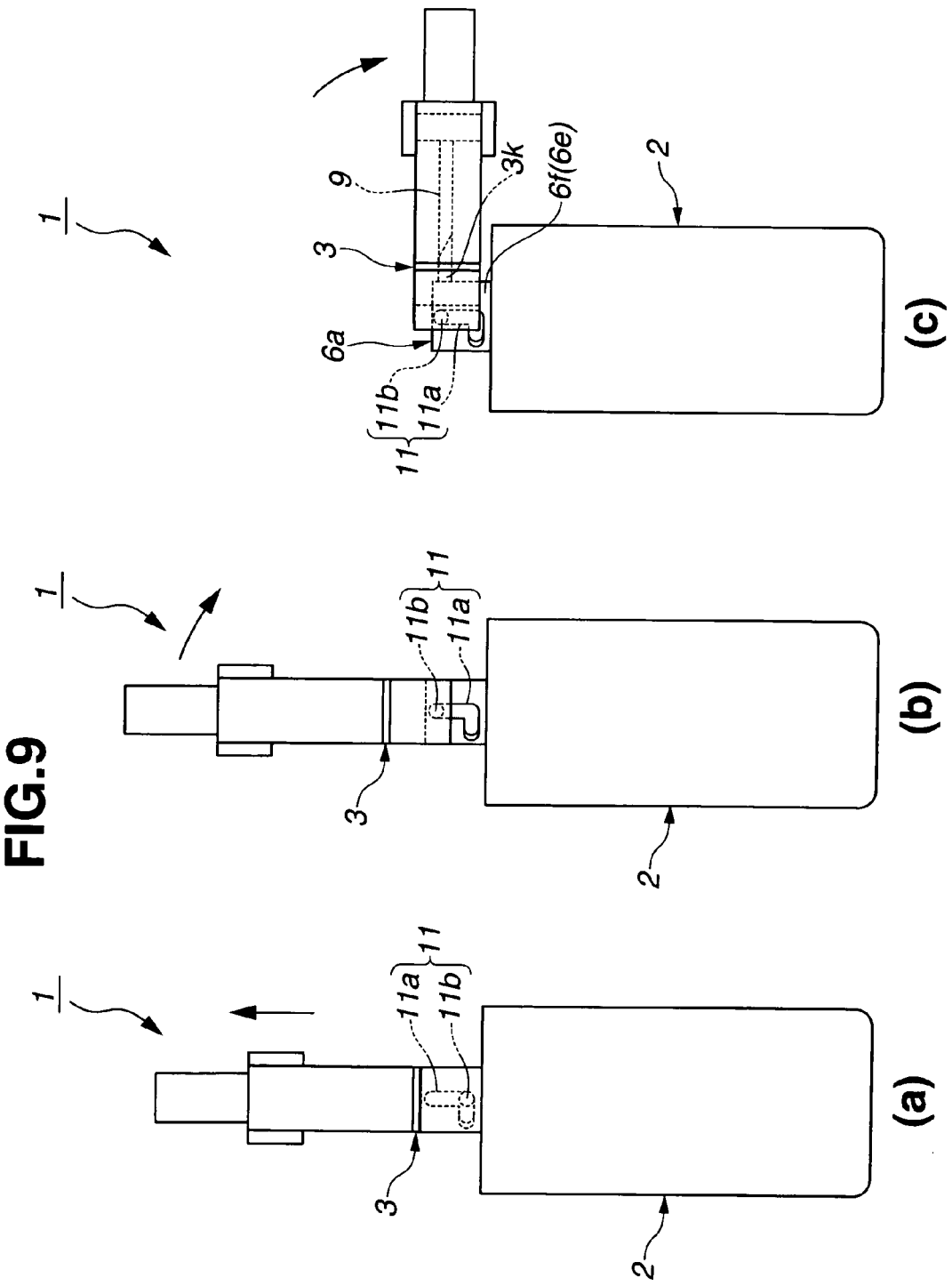
FIGS. 9(a)-(c) are a side view of the medicine sprayer according to the first embodiment of the present invention, and showing steps of relative movement of the first divided member and the second divided member.

In the protrusion 6a and the arm portions 3d and 3d (FIG. 3), there is a guide mechanism 11 (FIG. 4) arranged to define the relative movement of the body section 2 and the movable section 3. In this embodiment, as shown in FIGS. 2, 4 and 9, the guide mechanism 11 includes guide grooves 11a which are formed in the cylindrical outer surface 6f of the protrusion 6a; and protrusions 11b and 11b which are formed on the arm portion 3d, which have a substantially cylindrical shape, and which serve as guiding members arranged to be inserted into the guide grooves 11*a* and 11*a*. The guide grooves 11*a* and 11*a* are formed in a symmetrical (axially symmetry) manner with respect to the central axis C of the cylindrical protrusion 6*a*. The protrusions 11*b* and 11*b* protruding on the abutment surface between each of the arm portions 3*d* and 3*d* and the cylindrical outer surface 6*f* of the protrusion 6*a* are inserted, respectively, into the corresponding guide grooves 11*a* and 11*a*.

As shown in FIG. 4, the guide groove 11*a* has a substantially L-shape, and includes a circumferentially extending portion 11*c* extending in the circumferential direction; and an axially extending portion 11*d* extending in the axial direction of the cylindrical protrusion 6*a*.

Figure 5:
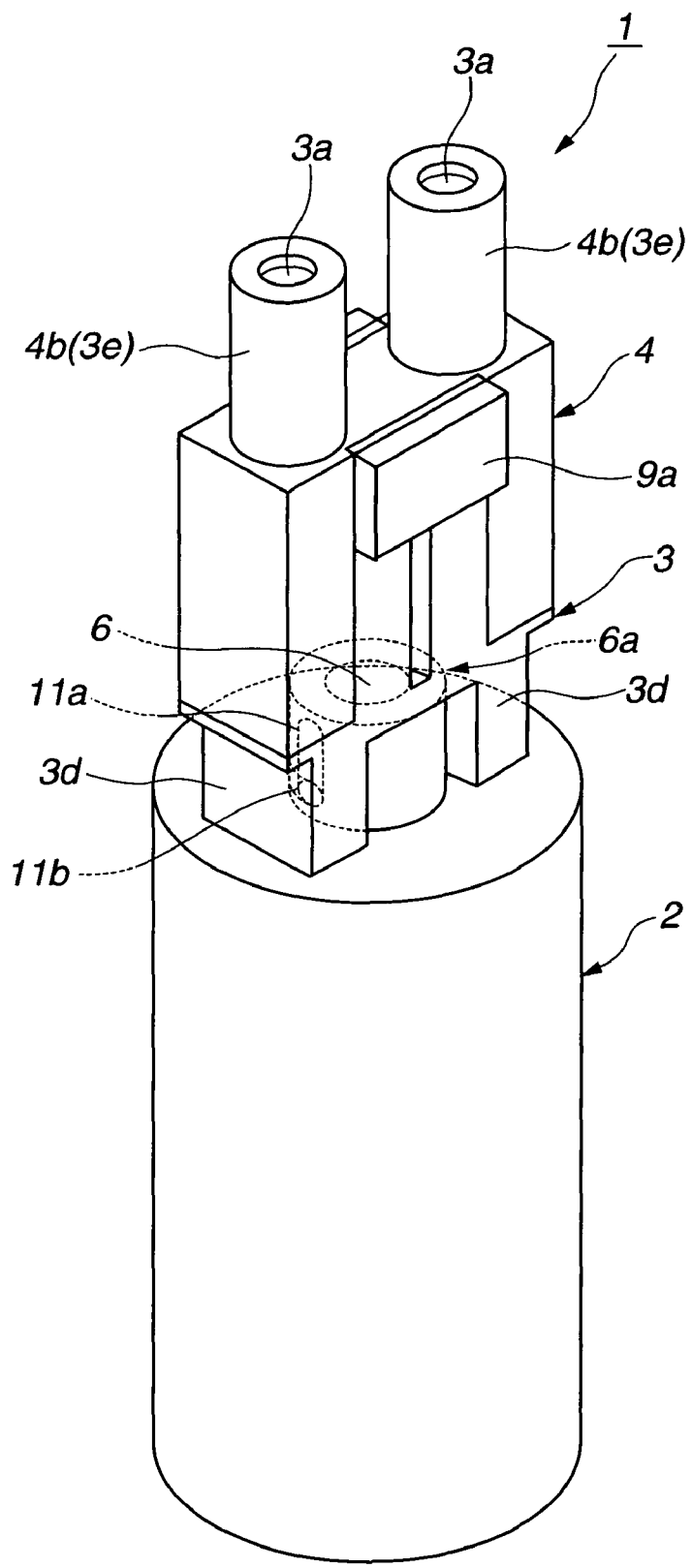
FIG. 5 is a perspective view of the medicine sprayer according to the first embodiment of the present invention, in which a second divided member is relatively pivoted with respect to a first divided member in a circumferential direction of a central axis.

The relative pivot movement about the central axis C of the body section 2 and the movable section 3 between the posture of FIG. 3 and the posture of FIG. 5 is defined by the movement of the protrusion 11*b* along the circumferentially extending portion 11*c*. The relative movement (approaching and separating movement) in the upward and downward directions of the body section 2 and the movable section 3 between the posture of FIG. 5 and the posture of FIG. 6 (between the posture of FIG. 9(*a*) and the posture of FIG. 9(*b*)) is defined by the movement of the protrusion 11*b* along the axially extending portion 11*d*.

Figure 6:
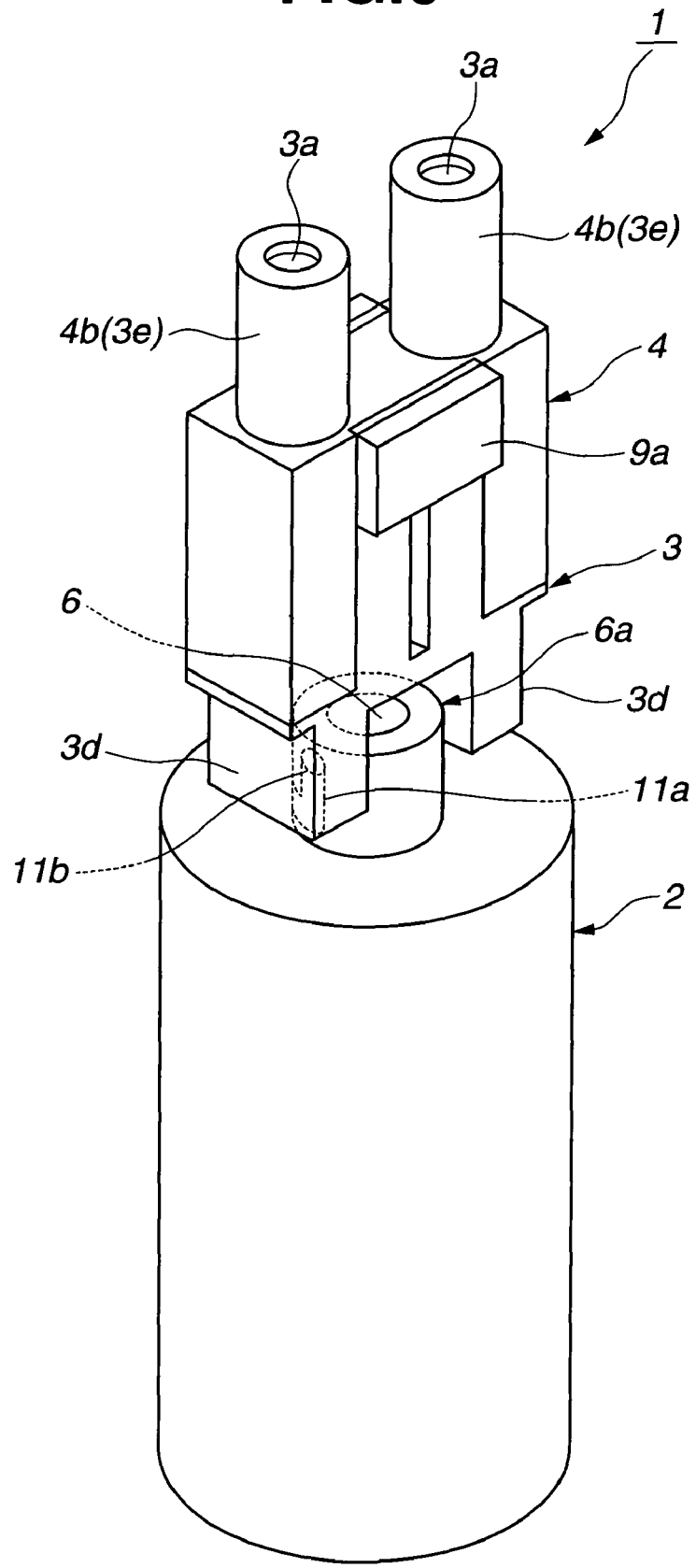
FIG. 6 is a perspective view of the medicine sprayer according to the first embodiment of the present invention, in which the second divided member is separated from the first divided member along the axis direction of the central axis.

Moreover, as shown in FIG. 6 (FIG. 9(*b*)) and FIG. 7 (FIG. 9(*c*)), the movable section 3 is pivoted (inclined) about the protrusions 11*b* with respect to the body section 2 while the force is applied and held in a direction (in the upward direction) in which the movable section 3 is separated from the body section 2 in a state in which the movable section 3 is separated from the body section 2 (in a state in which the protrusion 11*b* is located at a semi-cylindrical upper end 11*e* (FIG. 4) of the axially extending portion 11*d* in this embodiment). Consequently, the body section 2 and the movable section 3 are bent at substantially right angle.

FIGS. 2 and 3 show a spray enable state in which the medicine sprayer can spray the medicine 10 (FIG. 12) (the capsule 8 and the medicine 10 are omitted). In this state, the movable section 3 covers the capsule insertion hole 6 formed in the body section 2. As shown in FIG. 2, the end surface 2*d* of the body section 2 is abutted on the end surfaces 3*f* of the arm portions 3*d* and 3*d*. A bottom surface 3*g* between the two arm portions 3*d* and 3*d* of the movable section 3 is abutted on the end surface 6*g* of the protrusion 6*a*, and closes the opening portion 6*b* so as not to leak the medicine 10 (FIG. 12) from the boundary between the body section 2 and the movable section 3 to the outside. Moreover, in this state, a protrusion 3*h* formed on the bottom surface 3*g* is inserted from the opening portion 6*b* into the upper portion within the capsule insertion hole 6, so as to hold down the capsule 8 (FIG. 12) inserted into the capsule insertion hole 6, from the opposite side (the upper side) of the bottom surface 6*c* to squeeze into the bottom side of the capsule insertion hole 6. Accordingly, it is possible to improve the contact between the outer surface 8*a* of the capsule 8 and the bottom surface 6*c* and the inner circumferential surface 6*d* of the capsule insertion hole 6, and to further ensure the sealing of the medicine 10 at these portions. Moreover, a spherical recessed surface 3*i* is formed on the protrusion 3*h*, and fit on the semiround portion of the capsule 8. Accordingly, it is possible to further ensure the sealing of the medicine 10 at these portions.

In the medicine sprayer 1, in this state, the capsule puncture needle 9 is arranged to be moved through the opening portion 6*b* into the capsule insertion hole 6. That is, the capsule puncture needle 9 is received to extend on the central axis C of the capsule insertion hole 6 within a needle receiving portion 3*j* formed in the rigidity portion 3*c* of the movable section 3. A slider 9*a* on which the capsule puncture needle 9 is fixed is supported on the rigid portion 3*c* to move in the advancing and returning directions along the central axis C. Moreover, in this state, an outlet 3*k* of the capsule puncture needle 9 confronts the opening portion 6*b* of the capsule insertion hole 6. Accordingly, as shown in FIG. 11, the slider 9*a* supported on the rigid portion 3*c* to be slid in the advancing and returning directions are slid toward the body section 2 (the lower side) by the fingers and so on in a state in which the capsule 8 is inserted into the capsule insertion hole 6 as shown in FIG. 10. Consequently, the capsule puncture needle 9 fixed on the slider 9*a* enters from the outlet 3*k* into the capsule insertion hole 6. As shown in FIG. 12, the punctures 8*b* are formed in the capsule 8. Moreover, in this embodiment, by the movement of the capsule puncture needle 9, the two punctures 8*b* are formed, respectively, at upper and lower portions (the two portions on the medicine receiving chamber 7's side and on the opposite side of the medicine receiving chamber 7). As shown in FIG. 12, a seal member 12 is mounted at a position corresponding to the position of the end portion of the capsule puncture needle 9 in a state in which the capsule puncture needle 9 is received in the needle receiving portion 3*j*, so as to suppress the leakage of the air and the medicine 10 around the capsule puncture needle 9.

On the other hand, FIGS. 6, 7, 8, 9(*b*), and 9(*c*) show a spray disable state in which the medicine 10 can not be sprayed. In particular, in a state of FIGS. 7, 8 and 9(*c*), the capsule insertion hole 6 formed in the body section 2 is not covered by the movable section 3, and exposed to the outside. As shown in FIG. 8, it is possible to insert the capsule 8 through the opening portion 6*b* into the capsule insertion hole 6. In this state, the body section 2 and the movable section 3 are in the bent posture in which the body section 2 and the movable section 3 are bent at the substantially right angle. Consequently, the outlet 3*k* of the capsule puncture needle 9 from the movable section 3 confronts the cylindrical outer surface 6*f* of a side wall 6*e* of the protrusion 6*a* of the body section 2. By this side wall 6*e*, it is possible to limit restrict the movement of the capsule puncture needle 9 to the outside.

As shown in FIG. 2, within the rigid portion 3*c*, there are formed air passages 3*m* and 3*n* arranged to connect the capsule insertion hole 6 and the discharge holes 3*a*. The air passage 3*m* connected with the capsule insertion hole 6 extends in the upward and downward directions along the central axis C, and serves as a passage for the advancing and the returning movement of the capsule puncture needle 9. An opening portion of the air passage 3*m* on the recessed surface 3*i* is the outlet 3*k* of the capsule puncture needle 9. The air passages 3*n* and 3*n* are connected with this air passage 3*m*. Each of the air passages 3*n* and 3*n* includes a portion extending in a direction crossing the air passage 3*m* (in a substantially horizontal direction in the still standing state). Each of the air passages 3*n* and 3*n* is bent from an end portion of the portion of that air passage 3*n* which is farther from the central axis C, toward one of the insertion portions 3*e* and 3*e* (in the upward direction). The air passages 3*n* and 3*n* extend in parallel to each other, and are connected, respectively, with the discharge holes 3*a* and 3*a*. In this embodiment, the needle receiving portion 3*j* is disposed between the air passages 3*n* and 3*n* in parallel to the air passages 3*n* and 3*n*. The needle receiving portion 3*j* and the two air passages 3*n* and 3*n* are effectively disposed.

Hereinafter, operation of spraying the medicine of the medicine sprayer 1 having the above-described structure will be illustrated. First, in the state of FIGS. 7, 8 and 9(*c*), the capsule 8 is inserted into the capsule insertion hole 6 which is not covered by the movable section 3, and which is exposed to the outside. Subsequently, the movable section 3 is raised up as shown in FIGS. 6 and 9(b). Then, the movable section 3 is moved in the downward direction to become the state shown in FIGS. 5 and 9(a). The movable section 3 is pivoted in the circumferential direction to become the state shown in FIGS. 10 and 3 to be the spray enable state. During this period, in the guide mechanism 11, the protruding portions 11 serving as the guide member are moved within the guide grooves 11a in order of FIGS. 4(c)→(b)→(a). In this case, in the movement from FIG. 4(b) to FIG. 4(a), it is possible to understand that the circumferentially extending portions 11c of the guide grooves 11a serve as a lock mechanism arranged to lock the body section 2 and the movable section 3 in a direction along the central axis C.

Next, the slider 9a of the body section 2 is slid in the downward direction from the state shown in FIG. 10 to the state shown in FIG. 11 so as to form, by the capsule puncture needle 9, the punctures (through holes) 8b and 8b located at the upper and lower portions of the capsule 8. The slider 9a is slid in the upward direction to the state shown in FIG. 12 to return the capsule puncture needle 9 to receiving portion 3j.

In this state of FIG. 12, the outer wall 2b of the air chamber 2a is pressed by the fingers and so on, and the air within the air chamber 2a is discharged from the air passage 5. In this case, the medicine 10 within the capsule 8 and the medicine receiving chamber 7 is discharged with the air supplied by the pressure by the constriction of the air chamber 2a. The air passes through the annular groove portion 7b, the side holes 7c, the medicine receiving chamber 7, the puncture 8b, the inside of the capsule 8, the puncture 8b, the air passage 3m, and the air passages 3n which serve as the air passage 5, and is discharged from the discharge hole 3a. In this case, the stirred flow (swirl flow) is formed in the medicine receiving chamber 7, and the air and the medicine 10 are effectively mixed. Accordingly, the medicine 10 can surely reaches the bottom of the nasal cavity, and it is possible to suppress the medicine 10 from remaining in the medicine sprayer 1.

The medicine sprayer 1 according to this embodiment includes the outer skin section 4 which is detachable, and which is closely attached at an end portion of the medicine sprayer 1 which are formed with the discharge holes 3a. As shown in FIG. 14, this outer skin section 4 includes a main portion 4a covering the rigid portion 3c of the movable section 3 from the end portion; and cylindrical portions 4b protruding from the main portion 4a, and covering the insertion portions 3e. A cutaway portion 4c is formed in the main portion 4a, and arranged to avoid the interference with the movement space of the slider 9a. Each of the cylindrical portions 4b includes a through hole 4d formed at an end portion of that cylindrical portion 4b, and connected with one of the discharge holes 3a. Consequently, it is possible to readily keep the medicine sprayer 1 clean by changing the outer skin section 4, without cleaning the surface of the medicine sprayer 1.

In the above mentioned embodiment, the body section 2 is formed with the capsule insertion hole 6 arranged to hold the capsule 8. The movable section 3 includes the capsule puncture needle 9 arranged to be moved into or out of the capsule insertion hole 6. The body section 2 and the movable section 3 are connected with each other to be relatively moved at least between the posture in which at the capsule insertion hole 6 is exposed and the posture in which the capsule insertion hole is hid by the movable section 3. The body section 2 is arranged to restricts the advancing movement of the capsule puncture needle 9 in a state in which the body section 2 and the movable section 3 are in the posture in which the capsule insertion hole 6 is exposed. Accordingly, it is possible to suppress the capsule puncture needle 9 from exposing, and to further ensure the sanitary and the safety of the capsule puncture needle 9.

In this embodiment, the body section 2 and the movable section 3 are connected with each other to be relatively pivoted at least between the posture in which the capsule insertion hole 6 is exposed and the posture in which the capsule insertion hole 6 is hid. In the state in which the body section 2 and the movable section 3 are in the posture in which the capsule insertion hole 6 is hid, the outlet 3k of the capsule puncture needle 9 from the movable section 3 confronts the opening portion 6b of the capsule insertion hole 6, and the capsule puncture needle 9 can move into or out of the capsule insertion hole 6 from the opening portion 6b. In the state in which the body section 2 and the movable section 3 are in the posture in which the capsule insertion hole 6 is exposed, the outlet 3k confronts the outside of the side wall 6e of the capsule insertion hole 6, and the side wall 6e is arranged to restricts the advancing movement of the capsule puncture needle 9. Accordingly, it is possible to exemplify the structure in which the body section 2 restricts the exposure of the capsule puncture needle 9 from the movable section 3, by a relatively simple structure.

In this example, the capsule insertion hole 6 is the cylindrical hole of the cylindrical protrusion 6a formed in the body section 2. The pair of the arm portions 3d are formed in the movable section 3, and arranged to sandwich the protrusion 6a. The guide grooves 11a are formed in one of the protrusion 6a and the arm portions 3d. The protruding portions 11b are formed in the other of the protrusion 6a and the arm portions 3d, and arranged to serve as the guide member arranged to guide into the guide groove 11a. In the state in which the body section 2 and the movable section 3 are in the posture in which the capsule insertion hole 6 is hid, the end surface 6g of the protrusion 6a and the bottom surface 3g between the pair of the arm portions 3d and 3d are abutted on each other, and the bottom surface 3g is arranged to close the opening portion 6b of the capsule insertion hole 6. Each of the guide groove 11a includes the axially extending portion 11d arranged to extend in a direction in which the end surface 6g and the bottom surface 3g are abutted on and separated from each other. When the body section 2 and the movable section 3 are changed from the posture in which the capsule insertion hole 6 is hid to the posture the capsule insertion hole 6 is exposed, the end surface 6g and the bottom surface 3g are separated from each other. Accordingly, it is possible to ensure the sealing characteristic of the opening portion 6b of the capsule insertion hole 6, and to exemplify the mechanism in which the body section 2 and the movable section 3 are separated from each other to be readily relatively pivoted from each other, by the relatively simple structure.

Second Embodiment

Figure 15:
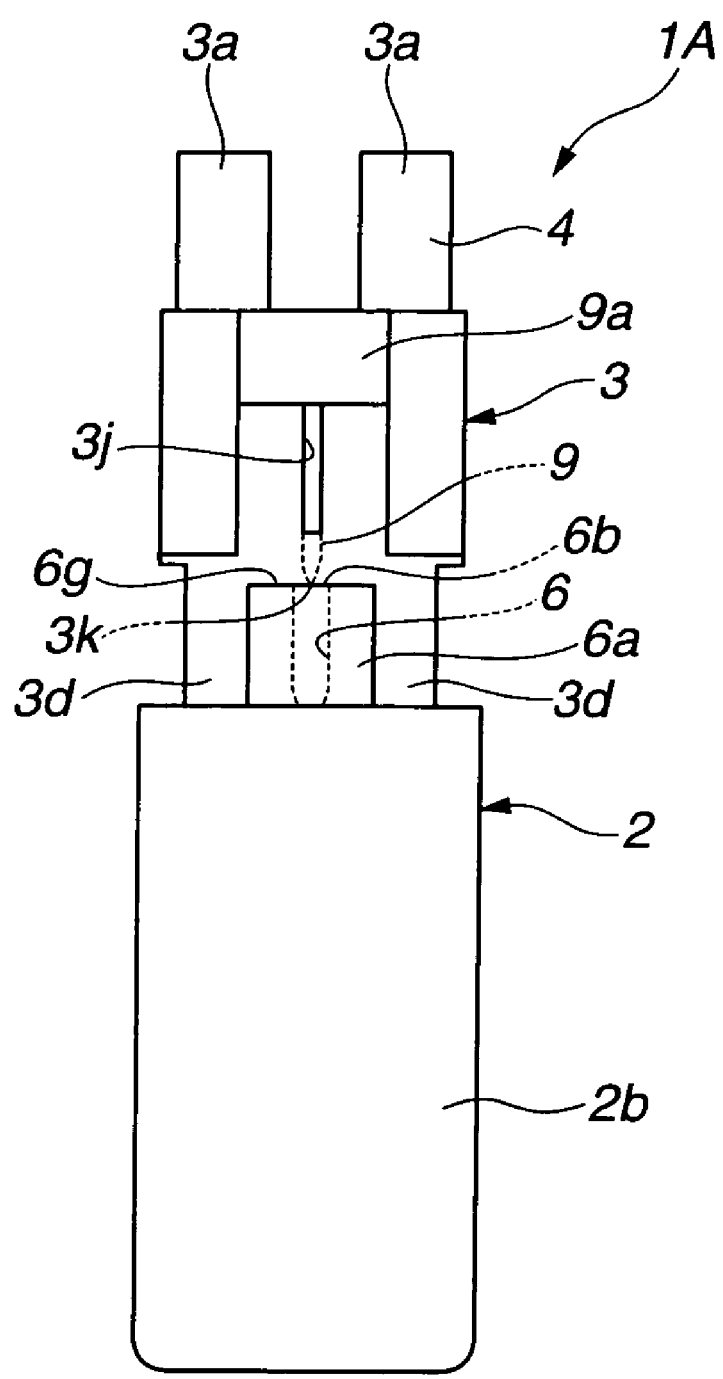
FIG. 15 is a front view showing an appearance of a medicine sprayer according to a second embodiment of the present invention.
Figure 16:
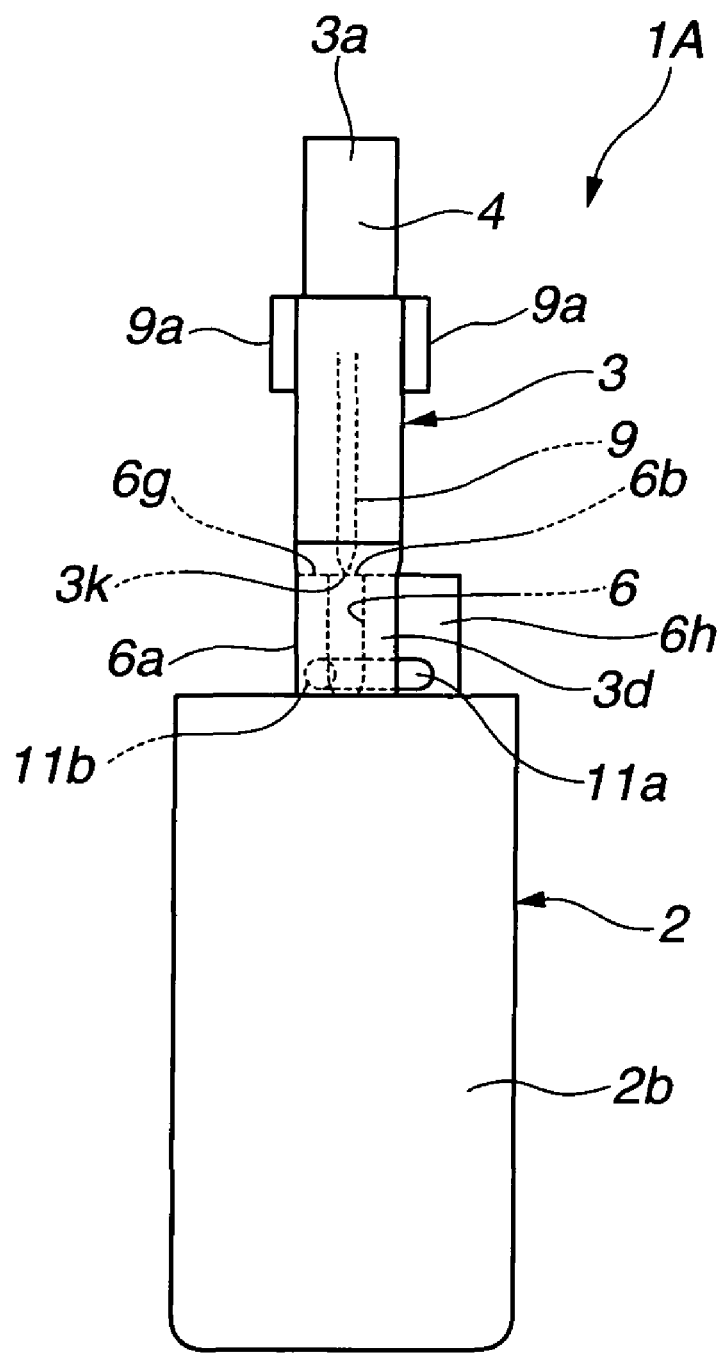
FIG. 16 is a side view showing an appearance of a medicine sprayer according second embodiment of the present invention.
Figure 17:
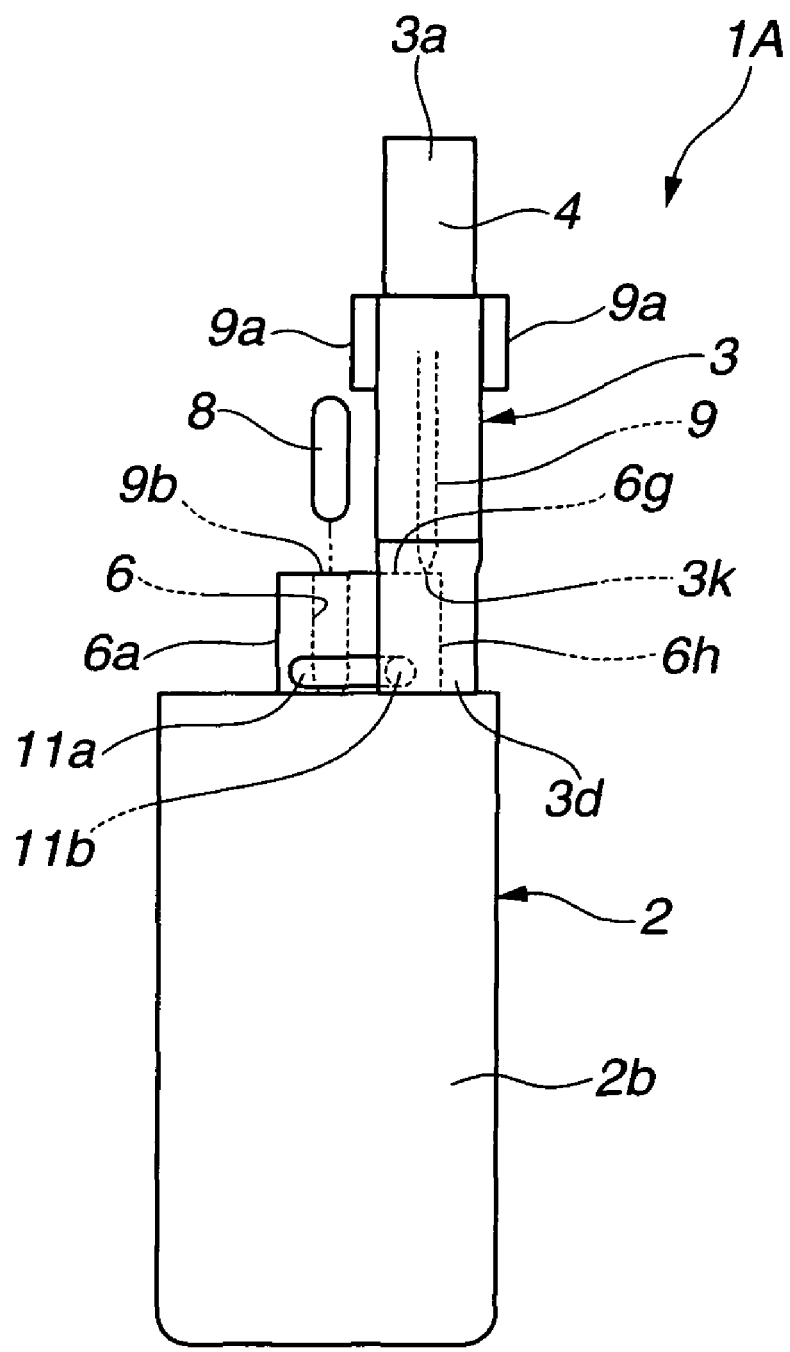
FIG. 17 is a side view showing a relative slide state between a first divided member and a second divided member of the medicine sprayer according to the second embodiment of the present invention.

FIGS. 15-16 show a second embodiment of the present invention. The structure of the second embodiment is substantially identical to the structure of the first embodiment in most aspects as shown by the use of the same reference numerals. The repeated illustrations are omitted. FIG. 15 is a front view showing an appearance of a medicine sprayer according to this embodiment. FIG. 16 is a side view showing an appearance of the medicine sprayer according to the this embodiment. FIG. 17 is a side view showing a relative sliding state of the first divided member and the second divided member. In this embodiment, the medicine sprayer is also a powder medicine administrating apparatus for administrating the powder medicine into the nasal cavity.

The medicine sprayer 1A according to this embodiment has a structure substantially identical to the structure of the first embodiment, as shown in FIG. 15. The medicine sprayer 1A includes a body section 2 serving as the first divided member, and a movable section 3 serving as the second divided member connected to be relatively moved (relatively slid) with respect to the body section 2.

The capsule insertion hole 6 is formed in the body section 2, and arranged to serve as a capsule holding portion. The body section 2 and the movable section 3 are connected to be relatively slid at least between the posture in which the capsule insertion hole 6 is exposed as shown in FIG. 17, and the posture in which the capsule insertion hole 6 is hid as shown in FIG. 16.

In the state in which the body section 2 and the movable section 3 are in the posture in which the capsule insertion hole 6 is hid, the outlet 3k (cf. FIG. 2) of the capsule puncture needle 9 from the movable section 3 confronts the opening portion 6b of the capsule insertion hole 6, and the capsule puncture needle 9 can be moved into or out of the capsule insertion hole 6 from the opening portion 6b (cf. FIG. 2).

In the state in which the body section 2 and the movable section 3 are in the posture in which the capsule insertion hole 6 is exposed, the outlet 3k confronts the upper wall of the capsule insertion hole 6, that is, the end surface 6g of the protrusion 6a, and the end surface 6g is arranged to restricts the advancing movement of the capsule puncture needle 9. The capsule insertion hole 6 is formed in the cylindrical protrusion 6a protruding from the body section 2, like the first embodiment. The capsule insertion hole 6 is the cylindrical hole of the protrusion 6a.

The pair of the arm portions 3d are provided to the movable section 3, and arranged to sandwich the protrusion 6a. The guide grooves 11a are formed in right and left side surfaces (in the rightward and leftward directions of FIG. 15) of the protrusion 6a for the relatively sliding movement, and the guide grooves 11a extend in the forward and rearward directions (in the front and back directions of FIG. 15), as shown in FIG. 16. The protruding portions 11b are provided to the arm portion 3d, and arranged to be guided by the guide grooves 11a. The protruding portions 11b are slid within the guide grooves 11a, and the body section 2 and the movable section 3 can be relatively slid in the forward and rearward directions. In this case, the guide grooves 11a may be formed in the arm portion 3d, and the protruding portions 11b may be provided in the protrusion 6a.

In the state in which the body section 2 and the movable section 3 are in the posture in which the capsule insertion hole 6 is hid as shown in FIG. 16, the end surface 6g of the protrusion 6a and the bottom surface 3g (cf. FIG. 2) between the pair of the arm portions 3d are abutted on each other, and the bottom surface 3g closes the opening portion 6b of the capsule insertion hole 6. The protrusion 6a includes an extension portion 6h extending in a direction in which the opening portion 6b of the capsule insertion hole 6 is deviated from the outlet 3k of the capsule puncture needle 9. When the body section 2 and the movable section 3 are brought from the posture in which the capsule insertion hole 6 is hid (cf. FIG. 16) to the posture in which the capsule insertion hole 6 is exposed (cf. FIG. 17), the opening portion 6b and outlet 3k are separated from each other.

In the medicine spraying operation of the medicine sprayer 1A, the capsule 8 is fit into the capsule insertion hole 6 which is exposed to the outside, and which is not covered by the movable section 3, in the state of FIG. 17. The movable section 3 is slid along the guide groove 11a as shown in FIG. 16. The bottom surface 3g of the arm portions 3d closes the opening portion 6b of the capsule insertion hole 6. In this state, the medicine sprayer 1A becomes the spraying enable state. Subsequently, the slider 9a of the body section 2 is slid in the downward direction, and the capsule puncture needle 9 forms the punctures at the upper portion and the lower portion of the capsule 8, like the first embodiment. Then, the slider 9a is slid in the upward direction to the original state (cf. FIG. 15), so that the capsule puncture needle 9 is returned to the needle receiving portion 3j.

In the medicine sprayer 1A according to this embodiment, the body section 2 and the movable section 3 are connected to be relatively slid. When the body section 2 and the movable section 3 are in the posture in which the capsule insertion hole 6 is exposed, the outlet 3k of the capsule puncture needle 9 confronts the end surface 6g of the capsule insertion hole 6. Accordingly, it is possible to exemplify the structure in which the body section 2 is arranged to restrict the advancing movement of the capsule puncture needle 9 in connection with the sliding movement of the body section 2 and the movable section 3, by the further simple structure.

Moreover, in the state in which the protruding portions 11b are guided by the guide grooves 11a, the end surface 6g of the protrusion 6a and the bottom surface 3g between the pair of the arm portions 3d are abutted on each other. Accordingly, it is possible to ensure the sealing characteristic at this portion. In the state in which the protrusions 11b are guided within the guide grooves 11a in the extension portion 6h extending in the direction in which the end surface 6g of and the bottom surface 3g are deviated, the end surface 6g and the bottom surface 3g are separated from each other. Accordingly, it is possible to readily slide the body section 2 and the movable section 3.

Third Embodiment

Figure 18:
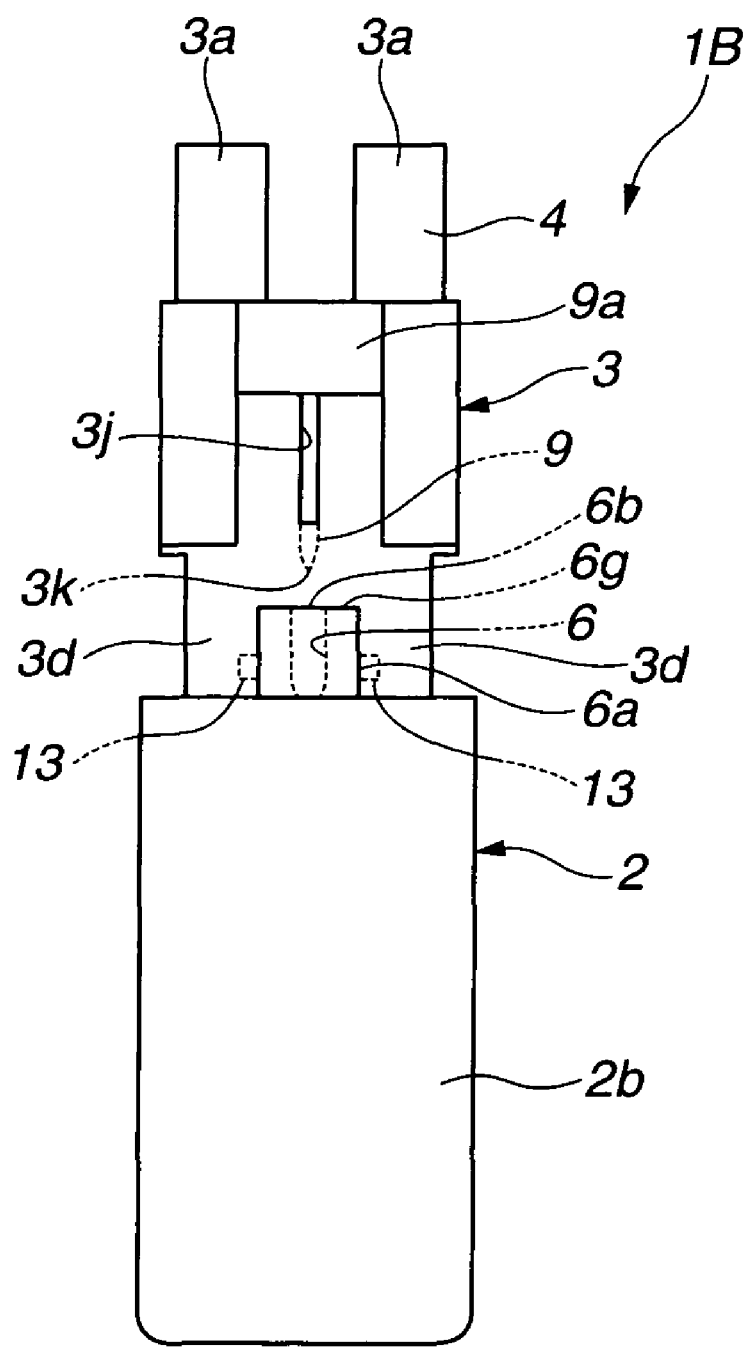
FIG. 18 is a front view showing an appearance of a medicine sprayer according to a third embodiment of the present invention.
Figure 19:
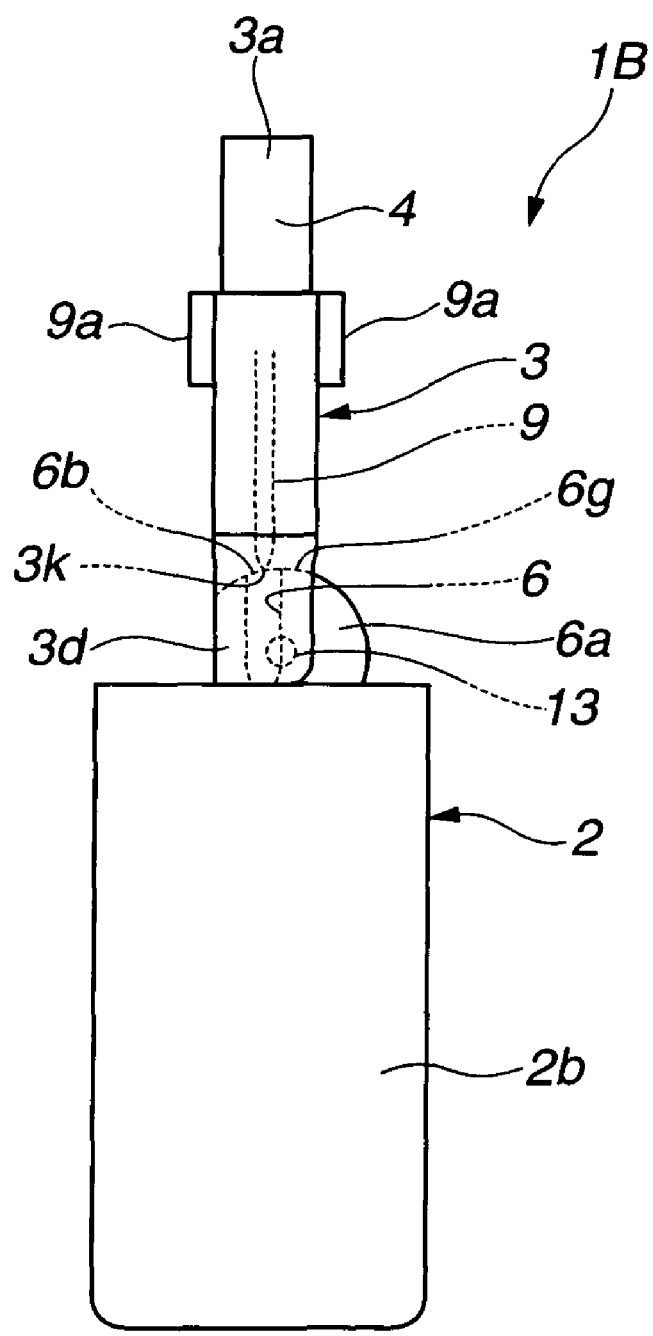
FIG. 19 is a side view showing the appearance of a medicine sprayer according to a third embodiment of the present invention.
Figure 20:
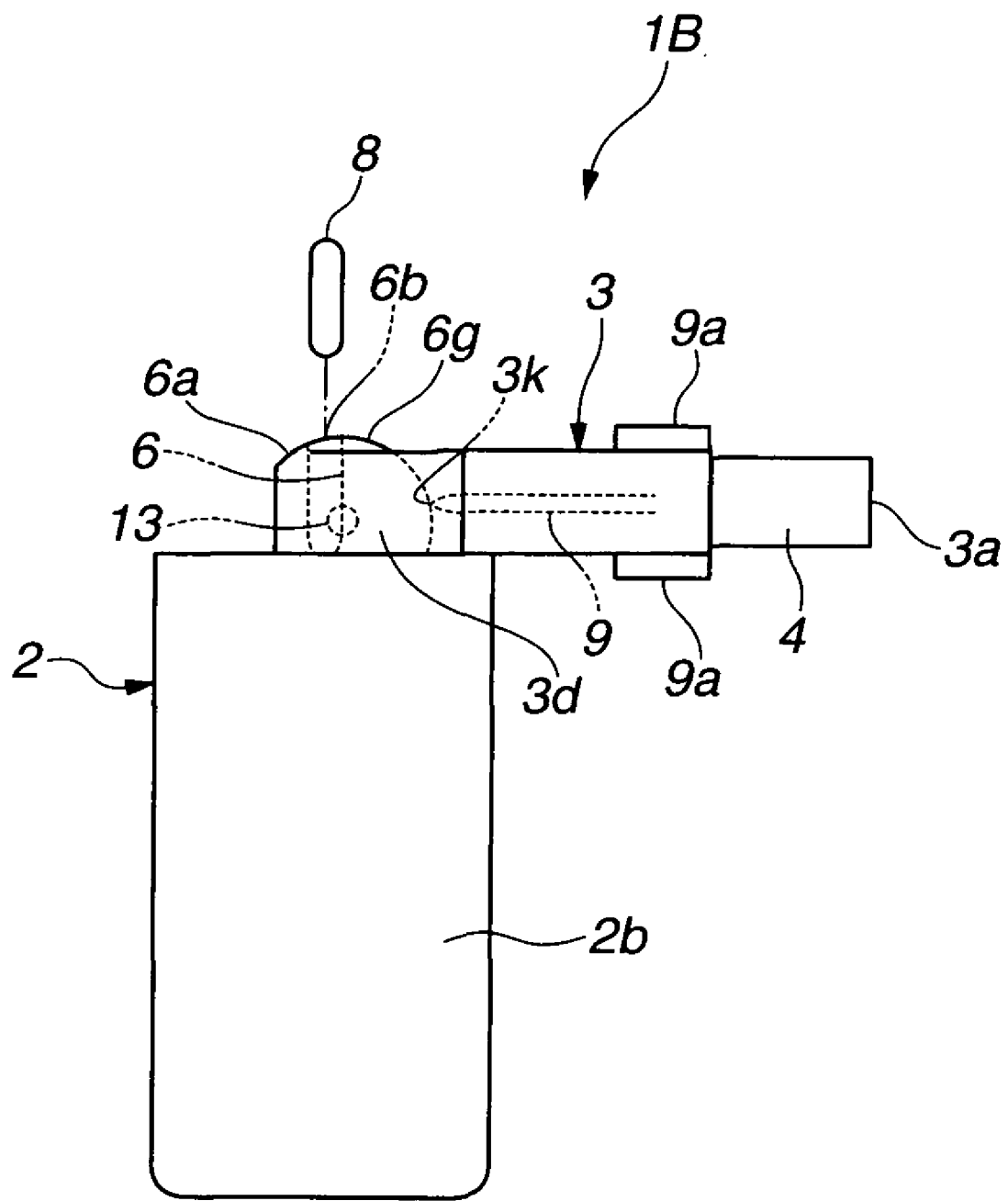
FIG. 20 is a side view showing a relative inclining state of the first divided member and the second divided member of the medicine sprayer according the third embodiment of the present invention.

FIGS. 18-20 show a third embodiment of the present invention. The structure of the third embodiment is substantially identical to the structure of the first embodiment in most aspects as shown by the use of the same reference numerals. The repeated illustrations are omitted. FIG. 18 is a front view showing an appearance of a medicine sprayer according to this embodiment. FIG. 19 is a side view showing the appearance of the medicine sprayer according to this embodiment. FIG. 20 is a side view showing a relatively inclining state of the first divided member and the second divided member. In this embodiment, the medicine sprayer is also a powder medicine administrating apparatus for administrating the powder medicine into the nasal cavity.

The medicine sprayer 1B according to this embodiment has a structure substantially identical to the structure of the first embodiment, as shown in FIG. 18. The medicine sprayer 1B includes a body section 2 serving as the first divided member, and a movable section 3 serving as the second divided member connected to be relatively moved (relatively inclined) with respect to the body section 2.

The capsule insertion hole 6 is formed in the body section 2, and arranged to serve as a capsule holding portion. The body section 2 and the movable section 3 are connected to be relatively inclined at least between the posture in which the capsule insertion hole 6 is exposed as shown in FIG. 20, and the posture in which the capsule insertion hole 6 is hid as shown in FIG. 19.

In the state in which the body section 2 and the movable section 3 are in the posture in which the capsule insertion hole 6 is hid, the outlet 3k (cf. FIG. 2) of the capsule puncture needle 9 from the movable section 3 confronts the opening portion 6b of the capsule insertion hole 6, and the capsule puncture needle 9 can be moved into or out of the capsule insertion hole 6 from the opening portion 6*b* (cf. FIG. 2).

In the state in which the body section 2 and the movable section 3 are in the posture in which the capsule insertion hole 6 is exposed, the outlet 3*k* confronts the outside of the side wall 6*e* of the capsule insertion hole 6, and the side wall 6*e* is arranged to restrict the advancing movement of the capsule puncture needle 9. The protrusion 6*a* is formed into a substantially semiround shape as viewed from the side, as shown in FIG. 19. The protrusion 6*a* has the side wall 6*e* located on the lateral side of the outer circumferential surface.

A pair of arm portions 3*d* are provided to the movable section 3 as shown in FIG. 18, and arranged to sandwich the protrusion 6*a*. These arm portions 3*d* can be pivoted by pin portions 13 protruding from a center portion of the semiround protrusion 6*a*. The movable section 3 can be inclined about the pin portions 13 as shown in FIG. 20.

In the medicine spraying operation of the medicine sprayer 1B, the movable section 3 is inclined about the pin portions 13 as shown in FIG. 20, so that the capsule insertion hole 6 covered by the movable section 3 is exposed to the outside. The capsule 8 is fit into the capsule insertion hole 6, and the movable section 3 is pivoted as shown in FIG. 19, and raised up in the initial position. The bottom surface 3*g* of the arm portions 3*d* closes the opening portion 6*b* of the capsule insertion hole 6.

In this state, the medicine sprayer 1A becomes the spraying enable state. Subsequently, the slider 9*a* of the body section 2 is slid in the downward direction, and the capsule puncture needle 9 forms the punctures at the upper portion and the lower portion of the capsule 8, like the first embodiment. Then, the slider 9*a* is slid in the upward direction to the original state (cf. FIG. 18), so that the capsule puncture needle 9 is returned to the needle receiving portion 3*j*.

In the medicine sprayer 1B according to this embodiment, the body section 2 and the movable section 3 are connected to be relatively inclined. When the body section 2 and the movable section 3 are in the posture in which the capsule insertion hole 6 is exposed, the outlet 3*k* of the capsule puncture needle 9 confronts the side wall 6*e* of the capsule insertion hole 6. Accordingly, it is possible to exemplify the structure in which the body section 2 is arranged to restrict the advancing movement of the capsule puncture needle 9 in connection with the relatively inclining movement of the body section 2 and the movable section 3, by the further simple structure.

Fourth Embodiment

Figure 21:
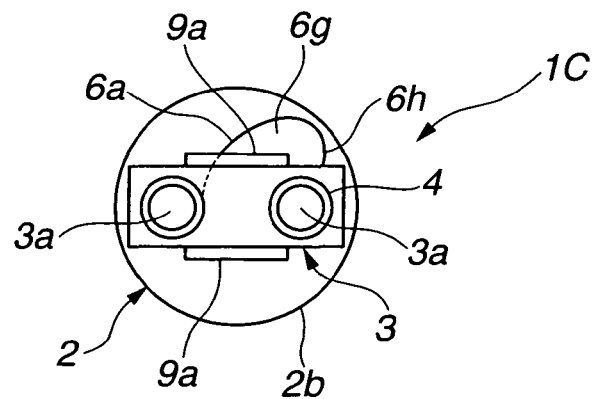
FIGS. 21(a) and 21(b) show a spraying state of a medicine sprayer according to a fourth embodiment of the present invention.
Figure 21:
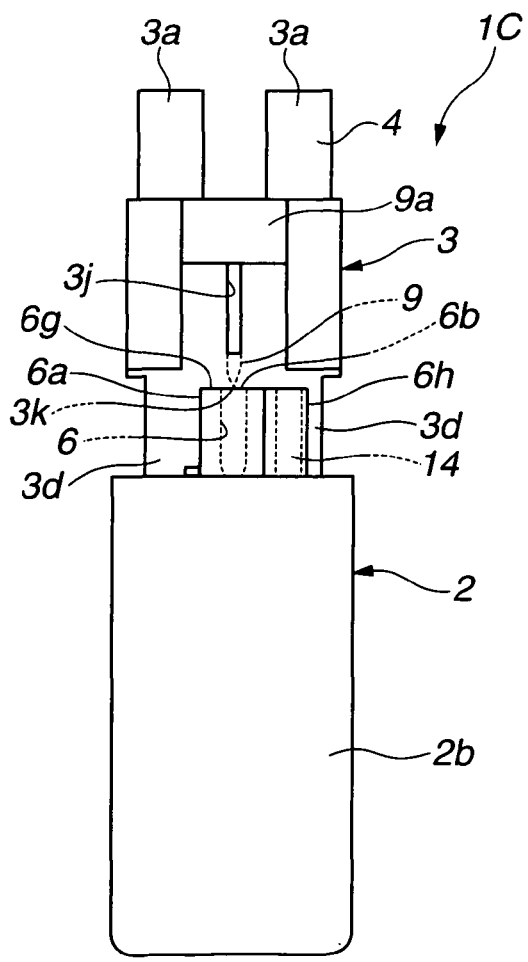
Figure 22:
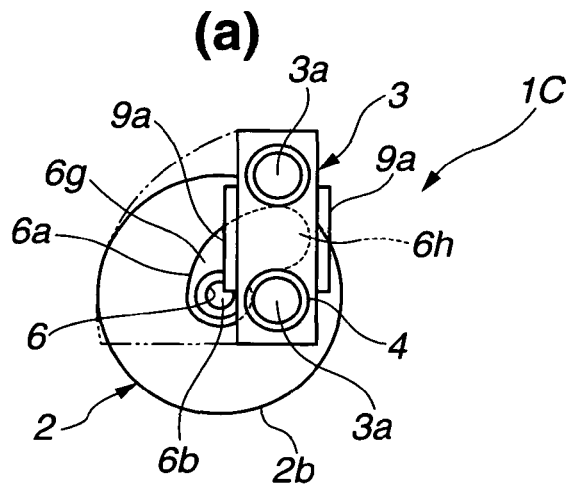
FIGS. 22(a) and 22(b) show a medicine administrating state of the medicine sprayer according to the fourth embodiment of the present invention.
Figure 22:
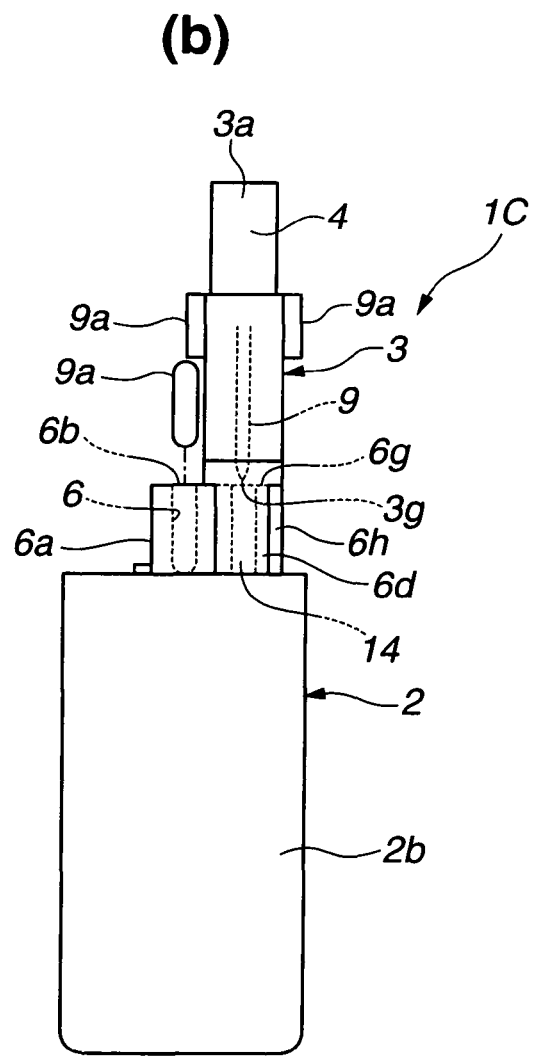

FIGS. 21 and 22 show a fourth embodiment of the present invention. The structure of the fourth embodiment is substantially identical to the structures of the first and second embodiments in most aspects as shown by the use of the same reference numerals. The repeated illustrations are omitted. FIG. 21 shows a spraying state of the medicine sprayer. FIG. 21(*a*) is a plan view. FIG. 21(*b*) is a front view. FIG. 22 shows a medicine administrating state of the medicine sprayer. FIG. 22(*a*) is a plan view. FIG. 22(*b*) is a front view. In this embodiment, the medicine sprayer is also a powder medicine administrating apparatus for administrating the powder medicine into the nasal cavity.

The medicine sprayer 1C according to this embodiment has a structure substantially identical to the structure of the second embodiment, as shown in FIG. 21. The medicine sprayer 1C includes a body section 2 serving as the first divided member, and a movable section 3 serving as the second divided member connected to be relatively moved (relatively slid) with respect to the body section 2.

The capsule insertion hole 6 is formed in the body section 2, and arranged to serve as a capsule holding portion. The body section 2 and the movable section 3 is connected to be relatively slid at least between the posture in which the capsule insertion hole 6 is exposed as shown in FIG. 22, and the posture in which the capsule insertion hole 6 is hid as shown in FIG. 21.

In the state in which the body section 2 and the movable section 3 are in the posture in which the capsule insertion hole 6 is hid, the outlet 3*k* (cf. FIG. 2) of the capsule puncture needle 9 from the movable section 3 confronts the opening portion 6*b* of the capsule insertion hole 6, and the capsule puncture needle 9 can be moved into or out of the capsule insertion hole 6 from the opening portion 6*b* (cf. FIG. 2).

In the state in which the body section 2 and the movable section 3 are in the posture in which the capsule insertion hole 6 is exposed, the outlet 3*k* confronts the end surface 6*g* of the capsule insertion hole 6, and the end surface 6*g* is arranged to restrict the advancing movement of the capsule puncture needle 9. The capsule insertion hole 6 is formed in the cylindrical protrusion 6*a* protruding from the body section 2, like the first embodiment. The capsule insertion hole 6 is the cylindrical hole of the protrusion 6*a*.

The pair of the arm portions 3*d* are provided to the movable section 3, and arranged to sandwich the protrusion 6*a*. One of the arm portions 3*d* (on the right side of FIG. 21) is mounted to the body section 2 to be pivoted by a rotation center shaft 14. The body section 2 and the movable section 3 can be relatively slid about the rotation center shaft 14.

In the state in which the body section 2 and the movable section 3 is in the posture in which the capsule insertion hole 6 is hid as shown in FIG. 21, the end surface 6*g* of the protrusion 6*a* and the bottom surface 3*g* (cf. FIG. 2) between the pair of the arm portions 3*d* are abutted on each other, and the bottom surface 3*g* closes the opening portion 6*b* of the capsule insertion hole 6. The protrusion 6*a* includes an extension portion 6*h* extending in a direction in which the opening portion 6*b* of the capsule insertion hole 6 is deviated from the outlet 3*k* of the capsule puncture needle 9. The extension portion 6*h* is formed into an arc shape whose a center is the rotation center shaft 14, in the plan view. The pair of the arm portions 3*d* are guided and slid on the both sides of the extension portion 6*h*. When the body section 2 and the movable section 3 are brought from the posture in which the capsule insertion hole 6 is hid (cf. FIG. 21) to the posture in which the capsule insertion hole 6 is exposed (cf. FIG. 22), the opening portion 6*b* and the outlet 3*k* are separated from each other.

In the medicine spraying operation of the medicine sprayer 1C, the capsule 8 is fit into the capsule insertion hole 6 which is exposed to the outside, and which is not covered by the movable section 3, in the state of FIG. 22. The movable section 3 is slid along the extension portion 6*h* of the protrusion 6*a* as shown in FIG. 21, so that the bottom surface 3*g* of the arm portions 3*d* closes the opening portion 6*b* of the capsule insertion hole 6. In this state, the medicine sprayer 1C becomes the spraying enable state. Subsequently, the slider 9*a* of the body section 2 is slid in the downward direction, and the capsule puncture needle 9 forms the punctures at the upper portion and the lower portion of the capsule 8, like the first embodiment. Then, the slider 9*a* is slid in the upward direction to the original state (cf. FIG. 21), so that the capsule puncture needle 9 is returned to the needle receiving portion 3*j*.

In the medicine sprayer 1C according to this embodiment, the body section 2 and the movable section 3 are connected to be relatively slid. When the body section 2 and the movable section 3 are in the posture in which the capsule insertion hole 6 is exposed, the outlet 3k of the capsule puncture needle 9 confronts the end surface 6g of the capsule insertion hole 6. Accordingly, it is possible to exemplify the structure in which the body section 2 is arranged to restrict the advancing movement of the capsule puncture needle 9 in connection with the relatively sliding movement of the body section 2 and the movable section 3, by the further simple structure.

Moreover, in the state in which the protruding portions 11b are guided by the guide grooves 11a, the end surface 6g of the protrusion 6a and the bottom surface 3g between the pair of the arm portions 3d are abutted on each other. Accordingly, it is possible to ensure the sealing characteristic at this portion. In the state in which the protrusions 11b are guided within the guide grooves 11a in the extension portion 6h extending in the direction in which the end surface 6g of and the bottom surface 3g are deviated, the end surface 6g and the bottom surface 3g are separated from each other. Accordingly, it is possible to readily slide the body section 2 and the movable section 3.

Fifth Embodiment

Figure 23:
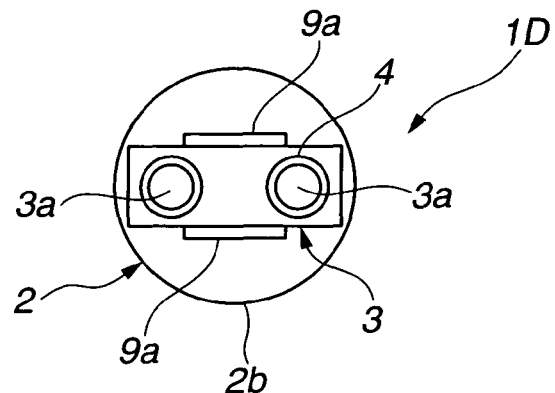
FIGS. 23(a) and 23(b) are views as viewed from a front, and showing the spraying state of the medicine sprayer according to a fifth embodiment of the present invention.
Figure 23:
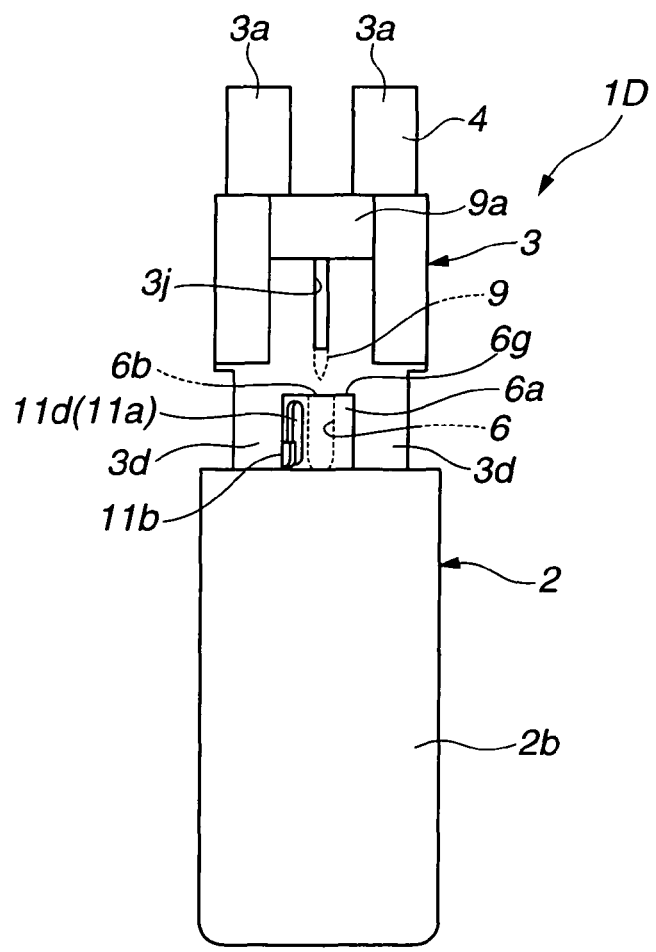
Figure 24:
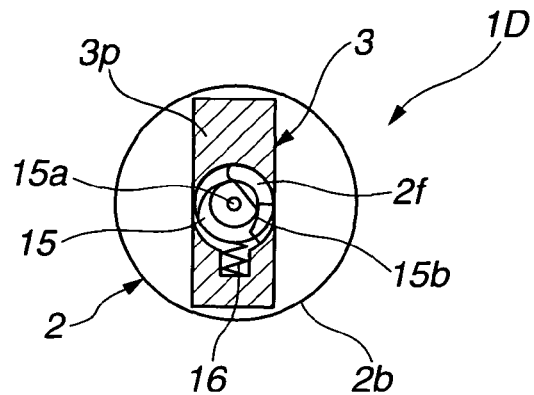
FIGS. 24(a) and 24(b) are views as viewed from a side, and showing the spraying state of a medicine sprayer according to a fifth embodiment of the present invention.
Figure 24:
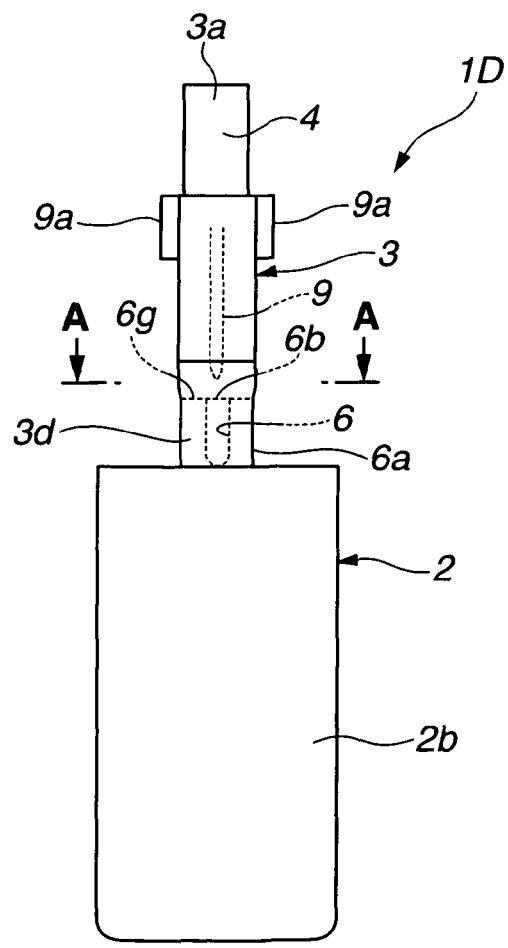
Figure 25:
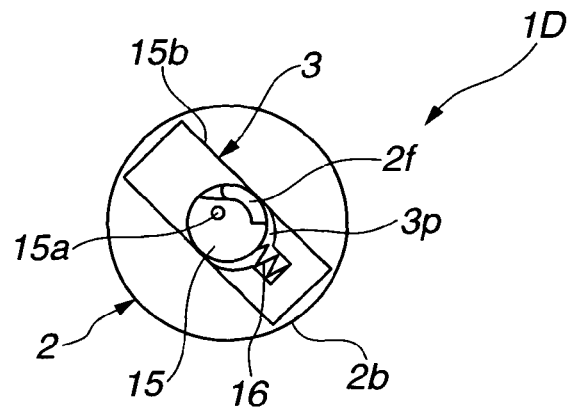
FIGS. 25(a) and (b) are views as viewed from a front, showing a medicine sprayer before the inclination, according to a fifth embodiment of the present invention.
FIG. 25(b) is a front view.
Figure 25:
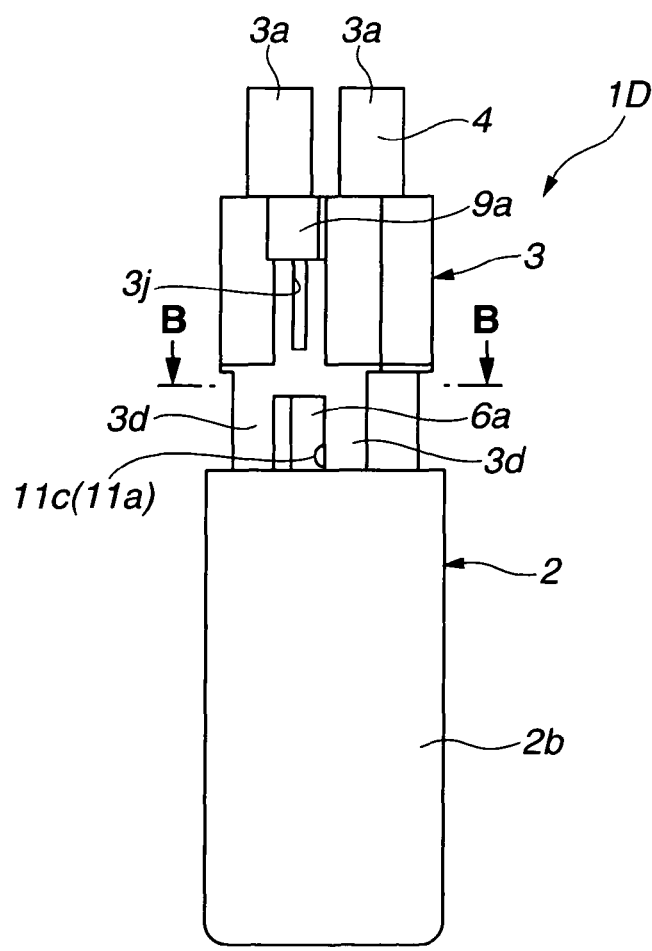
Figure 26:
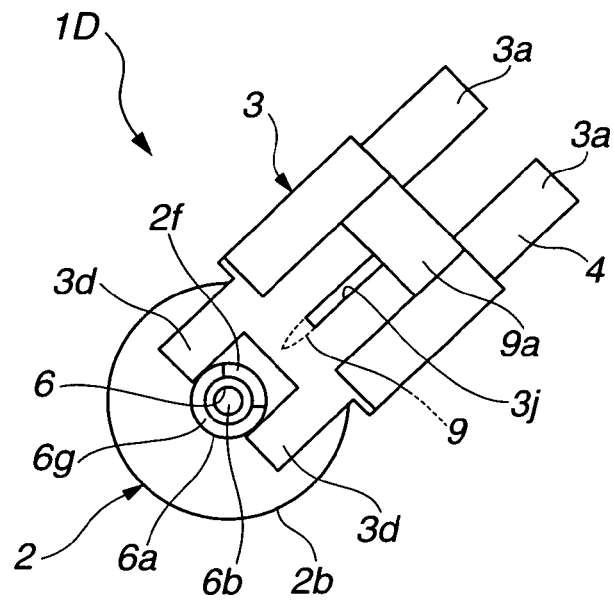
FIG. 26 is a plan view showing the inclined state of the medicine sprayer according to the fifth embodiment of the present invention.
Figure 27:
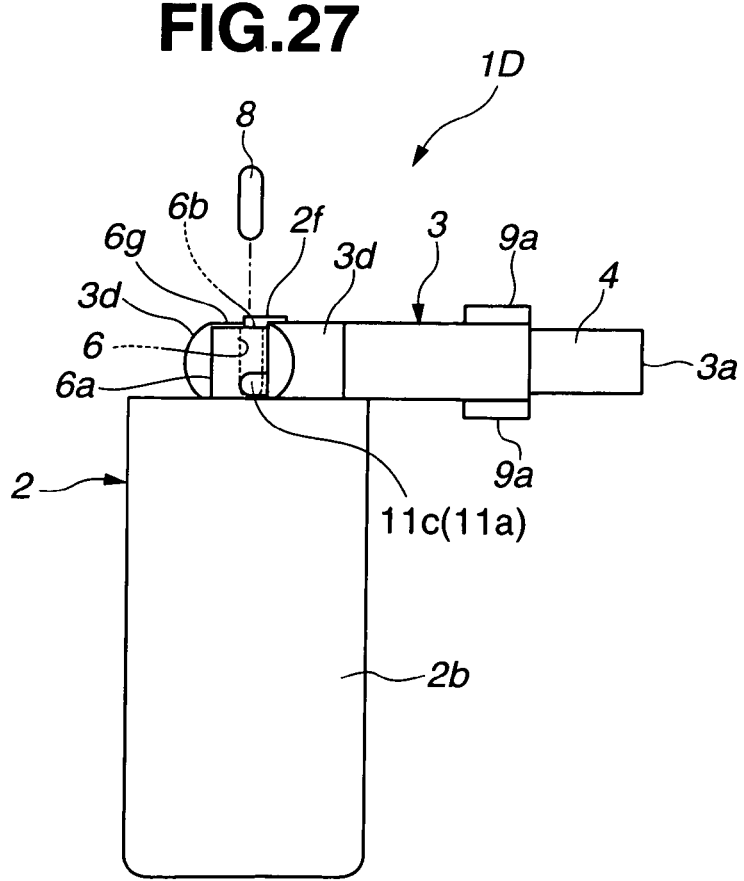
FIG. 27 is a front view showing the inclined state of the medicine sprayer according to the fifth embodiment of the present invention.

FIGS. 23-27 show a fifth embodiment of the present invention. The structure of the fifth embodiment is substantially identical to the structure of the first embodiment in most aspects as shown by the use of the same reference numerals. The repeated illustrations are omitted. FIG. 23 is a front view showing a spraying state of the medicine sprayer. FIG. 23(a) is a plan view. FIG. 23(b) is a front view. FIG. 24 is a side view showing the spraying state of the medicine sprayer. FIG. 24(a) is a sectional view taken along a line A-A of FIG. 24(b). FIG. 24(b) is a side view. FIG. 25 is a front view showing the medicine sprayer before the inclination. FIG. 25(a) is a sectional view taken along a line B-B of FIG. 25(b). FIG. 25(b) is a front view. FIG. 26 is a plan view showing the inclining state of the medicine sprayer. FIG. 27 is a front view showing the inclining state of the medicine sprayer. In this embodiment, the medicine sprayer is also a powder medicine administrating apparatus for administrating the powder medicine into the nasal cavity.

The medicine sprayer 1D according to this embodiment has a structure substantially identical to the structure of the first embodiment, as shown in FIG. 23. The medicine sprayer 1D includes a body section 2 serving as the first divided member, and a movable section 3 serving as the second divided member connected to be relatively moved (relatively slid) with respect to the body section 2.

The capsule insertion hole 6 is formed in the body section 2, and arranged to serve as a capsule holding portion. The body section 2 and the movable section 3 are connected to be relatively inclined at least between the posture in which the capsule insertion hole 6 is exposed as shown in FIGS. 26 and 27, and the posture in which the capsule insertion hole 6 is hid as shown in FIGS. 23 and 24. In this embodiment, the body section 2 and the movable section 3 have a state before the inclination which is between the posture in which the capsule insertion hole 6 is exposed and the posture in which the capsule insertion hole 6 is hid, and in which the movable section 3 is rotated with respect to the body section 2 a predetermined angle (substantially 45° in this embodiment).

In the state in which the body section 2 and the movable section 3 are in the posture in which the capsule insertion hole 6 is hid, the outlet 3k (cf. FIG. 2) of the capsule puncture needle 9 from the movable section 3 confronts the opening portion 6b of the capsule insertion hole 6, and the capsule puncture needle 9 can be moved into or out of the capsule insertion hole 6 from the opening portion 6b (cf. FIG. 2).

As shown in FIGS. 24 and 25, the movable section 3 includes a covering portion 15 arranged to cover the capsule insertion hole 6, and to move at the stage before the relative inclination of the body section 2 and the movable section 3. The covering portion 15 is arranged to restrict the advancing movement of the capsule puncture needle 9 at the stage before the relative inclination of the body section 2 and the movable section 3. The capsule insertion hole 6 is formed in the cylindrical protrusion 6a protruding from the body section 2, like the first embodiment. The capsule insertion hole 6 is the cylindrical hole of the protrusion 6a.

The covering portion 15 is formed into a substantially circular plate whose a part of an outer circumference portion is cut away. The covering portion 15 is received within a lower end portion of the movable section 3 in a state in which the medicine sprayer 1D still stands, that is, within a receiving chamber 3p formed below the capsule puncture needle 9, so as to be moved in a direction perpendicular to the central axis C.

The covering portion 15 includes a puncture hole 15a through which the capsule puncture needle 9 passes to the capsule insertion hole 6, in the state in which the capsule insertion hole 6 is hid by the movable section 3, that is, in the spraying state of the medicine sprayer shown in FIGS. 23 and 24. The covering portion 15 is arranged to move within the receiving chamber 3p, and to rotate as a unit with the movable section 3 about the central axis C of the movable section 3 by an engagement portion (not shown).

An arc restriction wall 2f protrudes from the body section 2, and is inserted into the receiving chamber 3p. The restriction wall 2f has a predetermined cam function, and is arranged to be mounted in the cutaway portion 15b of the covering portion 15. The inner chamber shape of the receiving chamber 3p is an oval shape extending in the movable direction of the covering portion 15. Between the receiving chamber 3p and the covering portion 15, there is provided a spring 16 arranged to press and urge the covering portion 15 in one direction, that is, in a direction in which the puncture hole 15a is deviated from the advancing movement of the capsule puncture needle 9.

The restriction wall 2f forcibly moves the covering portion 15 against the urging force of the spring 16 in the other direction (in the downward direction in the figure) when the movable section 3 is at the rotation position in the initial state (spraying state) so that the puncture hole 15a corresponds to the direction of the advancing movement of the capsule puncture needle 9. In this state, it is possible to perform the advancing movement of the capsule puncture needle 9. Moreover, the restriction wall 2f serves as a guide when the capsule 8 is inserted into the capsule insertion hole 6.

Next, when the movable section 3 is rotated to the stage before the inclination as shown in FIG. 25, the correction force of the covering portion 15 by the restriction wall 2f is released, the covering portion 15 is pushed in the one direction by the spring 16, and the puncture hole 15a is deviated from the direction of the advancing movement of the capsule puncture needle 9. In this state, the capsule puncture needle 9 is interrupted by the covering portion 15 to prevent the advancing movement. In this state in which the advancing movement of the capsule puncture needle 9 is prevented, the movable section 3 is inclined as shown in FIGS. 26 and 27. In this case, the covering portion 15 is inclined with the movable section 3.

The guide grooves 11a are formed in an outer cylindrical surface of the protrusion 6a, like the first embodiment (cf.

FIG. 4). Protruding portions 11b are formed in the arm portion 3d, and arranged to be inserted into the guide grooves 11a and 11a. The guide groove 11a is formed in a (axially) symmetrical manner with respect to the central axis of the cylindrical protrusion 6a. The protruding portions 11b protrude on the abutment surface between the arm portions 3d and 3d and the cylindrical outer surface of the protrusion 6a, and are inserted, respectively, into the corresponding guide grooves 11a.

Each of the guide grooves 11a includes a circumferentially extending portion 11c extending in the circumferential direction partially as shown in FIGS. 25 and 27, and an axially extending portion 11d extending in the axial direction of the cylindrical protrusion 6a. Each of the guide grooves 11a is formed into a substantially L-shape.

The relative pivot movement of the body section 2 and the movable section 3 about the central axis C between the posture of FIG. 23 and the posture of FIG. 25 is defined by the movement of the protruding portion 11b along the circumferentially extending portion 11c. The relative inclination of the body section 2 and the movable section 3 between the posture of FIG. 25 and the posture of FIG. 27 is defined by the movement of the protruding portion 11b along the axially extending portion 11d. In this case, the movable section 3 is inclined about the protruding portion 11b with respect to the body section 2, the body section 2 and the movable section 3 can be bent at a substantially right angle. In this case, the guide groove 11a may be formed in the arm portion 3d, and the protruding portion 11b may be formed in the protrusion 6a.

In the medicine spraying operation of the medicine sprayer 1D, the capsule 8 is fit into the capsule insertion hole 6 which is exposed to the outside, and which is not covered by the movable section 3, in the state of FIGS. 26 and 27. The movable section 3 in the inclined state is raised as shown in FIG. 25. Then, the movable section 3 is rotated about the central axis C to return to the initial state as shown in FIGS. 23 and 24. In this state, the bottom surface 3g of the arm portion 3d closes the opening portion 6b of the capsule insertion hole 6 to become the spray enable state. Subsequently, the slider 9a of the body section 2 is slid in the downward direction, and the capsule puncture needle 9 forms the holes at the upper portion and the lower portion of the capsule 8, like the first embodiment. Then, the slider 9a is slid in the upward direction to the original state (cf. FIG. 23), so that the capsule puncture needle 9 is returned to the needle receiving portion 3j.

Accordingly, in the medicine sprayer 1D according to this embodiment, the covering portion 15 restricts the advancing movement of the capsule puncture needle 9 at the stage (cf. FIG. 25) before the relative inclination of the body section 2 and the movable section 3. Accordingly, it is possible to suppress the capsule puncture needle 9 from exposing from the movable section 3 by the covering portion 15, except for the spraying state. Moreover, the covering portion 15 restricts the advancing movement of the capsule puncture needle 9 by the covering portion 15, and accordingly it is possible to smoothly incline the movable section 3 with respect to the body section 2.

The covering portion 15 allows the capsule puncture needle 9 to pass through the puncture holes 15a provided to the covering portion 15 in the posture in which the capsule insertion hole 6 is hid by the movable section 3, that is, in the spray state shown in FIGS. 23 and 24. Accordingly, it is possible to form the holes in the capsule 8 by the capsule puncture needle 9 at the spraying of the medicine in case of providing covering portion 15, like the above-mentioned embodiments.

The preferred embodiments of the present invention was illustrated above. However, the present invention is not limited to the above-mentioned embodiments. The present invention can varied in the various manner.

The present invention is applicable to a medicine sprayer arranged to discharge the powder medicine into the nasal cavity, the oral cavity and so on by the hand.

1, 1A, 1B, 1C, 1D medicine sprayer
2 body section (first divided member, air pump mechanism)
2a air chamber
3 movable section (second divided member)
3d arm portion
3g bottom surface
3k outlet
5 air passage
6 capsule insertion hole (capsule holding portion)
6b opening portion
6e side wall
6f cylindrical outer surface (outside)
6g end surface (upper side wall)
8 capsule
9 capsule puncture needle
10 medicine
11 guide mechanism
11a guide groove
11b protrusion
11d axially extending portion
15 covering portion
15a puncture hole

The invention claimed is:

1. A medicine sprayer comprising:
an air pump mechanism arranged to supply air by a pressure;
a capsule puncture needle arranged to form a hole in a capsule;
an air passage arranged to discharge a medicine within the capsule to outside the capsule, by the air supplied by the air pump mechanism;
a first divided member formed with a capsule holding portion holding the capsule;
a second divided member including the capsule puncture needle arranged to be moved into or out of the capsule holding portion;
the first divided member and the second divided member being connected to be relatively pivoted with respect to each other, at least between a posture in which the capsule holding portion is exposed, and a posture in which the capsule holding portion is hid by the second divided member,
the first divided member being arranged to restrict the advancing movement of the capsule puncture needle when the first divided member and the second divided member are in the posture in which the capsule holding portion is exposed,
wherein the first divided member includes a capsule insertion hole which serves as the capsule holding portion, and which is formed in a protrusion of the first divided member; an outlet of the capsule puncture needle from the second divided member confronts an opening portion of the capsule insertion hole when the first divided member and the second divided member are in the posture in which the capsule insertion is hid so that the capsule puncture needle is arranged to be moved from the opening portion into the capsule insertion hole; and the outlet confronts the protrusion of the first divided member when the first divided member and the second divided member are in the posture in which the capsule insertion hole is exposed so that the protrusion of the first divided member restricts the advancing movement of the capsule puncture needle.

2. The medicine sprayer as claimed in claim 1, wherein the capsule holding portion includes a bottom surface formed into a substantially semiround shape which is substantially closely attached to an end portion of the capsule.

3. The medicine sprayer as claimed in claim 1, wherein the medicine sprayer further comprises an outer skin section arranged to closely attached to an end portion formed with a discharge hole of the medicine, and to be detachable.

4. A medicine sprayer comprising:
an air pump mechanism arranged to supply air by a pressure;
a capsule puncture needle arranged to form a hole in a capsule;
an air passage arranged to discharge a medicine within the capsule to outside the capsule, by the air supplied by the air pump mechanism;
a first divided member formed with a capsule holding portion holding the capsule;
a second divided member including the capsule puncture needle arranged to be moved into or out of the capsule holding portion;
the first divided member and the second divided member being connected to be relatively pivoted at least between a posture in which the capsule holding portion is exposed, and a posture in which the capsule holding portion is hid by the second divided member,
the first divided member being arranged to restrict the advancing movement of the capsule puncture needle when the first divided member and the second divided member are in the posture in which the capsule holding portion is exposed,
wherein the first divided member includes a capsule insertion hole serving as the capsule holding portion; the first divided member and the second divided member are connected to be relatively pivoted at least between a posture in which the capsule insertion hole is exposed, and a posture in which the capsule insertion hole is hid; an outlet of the capsule puncture needle from the second divided member confronts an opening portion of the capsule insertion hole when the first divided member and the second divided member are in the posture in which the capsule insertion hole is hid so that the capsule puncture needle is arranged to be moved from the opening portion into the capsule insertion hole; and the outlet confronts an outer side of a side wall when the first divided member and the second divided member are in the posture in which the capsule insertion hole is exposed so that the side wall restricts the advancing movement of the capsule puncture needle.

5. The medicine sprayer as claimed in claim 4, wherein the first divided member includes a cylindrical protrusion; the capsule insertion hole is a cylindrical hole of the protrusion; the second divided member includes a pair of arm portions arranged to sandwich the protrusion; one of the protrusion, and the arm portions includes a guide groove; the other of the protrusion and the arm portions includes a guide member arranged to be guided in the guide groove; an end surface of the protrusion and a bottom surface between the pair of the arm portions are abutted on each other when the first divided member and the second divided member are in the posture in which the capsule insertion hole is hid so that the bottom surface closes the opening portion of the capsule insertion hole; the guide groove includes a portion extending in a direction in which the end surface and the bottom surface are abutted on or separated from each other so that the end surface and the bottom surface are separated from each other when the first divided member and the second divided member are changed from the posture in which the capsule insertion hole is hid to the posture in which the capsule insertion hole is exposed.

6. The medicine sprayer as claimed in claim 5, wherein the guide groove includes a portion extending substantially in a direction crossing a direction in which the end surface and the bottom surface are abutted on or separated from each other.

7. The medicine sprayer as claimed in claim 5, wherein the protrusion is formed into a cylindrical shape; the guide groove and the guide member are provided in a symmetrical manner with respect to a central axis of the protrusion; the guide member is mounted in the guide groove to serve as a pivot axis of the relative pivot of the first divided member and the second divided member.

8. The medicine sprayer as claimed in claim 4, wherein the capsule puncture needle is arranged to pass through the capsule held in the capsule insertion hole; a medicine receiving chamber is formed at an end portion of the capsule puncture needle passing through the capsule; the air passage is arranged to introduce the air supplied by the pressure from the air pump mechanism, into the medicine receiving chamber; and the air passage extends in a direction crossing a discharge direction of the medicine and the air from the medicine receiving chamber.

9. The medicine sprayer as claimed in claim 8, wherein the medicine receiving chamber is formed into a substantially cylindrical shape extending along an outer shape of the capsule; and the medicine receiving chamber includes a plurality of air passages connected in a tangent direction of an inner cylindrical surface, and arranged in a substantially winding shape.

10. A medicine sprayer comprising:
an air pump mechanism arranged to supply air by a pressure;
a capsule puncture needle arranged to form a hole in a capsule;
an air passage arranged to discharge a medicine within the capsule to outside the capsule, by the air supplied by the air pump mechanism;
a first divided member formed with a capsule holding portion holding the capsule;
a second divided member including the capsule puncture needle arranged to be moved into or out of the capsule holding portion;
the first divided member and the second divided member being connected to be relatively pivoted at least between a posture in which the capsule holding portion is exposed, and a posture in which the capsule holding portion is hid by the second divided member,
the first divided member being arranged to restrict the advancing movement of the capsule puncture needle when the first divided member and the second divided member are in the posture in which the capsule holding portion is exposed,
wherein the first divided member include a capsule insertion hole serving as the capsule holding portion; the first divided member and the second divided member are connected to be relatively inclined at least between a posture in which the capsule insertion hole is exposed, and a posture in which the capsule insertion hole is hid; an outlet of the capsule puncture needle from the second divided member confronts an opening portion of the capsule insertion hole when the first divided member and the second divided member are in the posture in which the capsule insertion hole is hid so that the capsule puncture needle is arranged to be moved from the opening portion into the capsule insertion hole; and the outlet confronts an outer side of a side wall of the capsule insertion hole when the first divided member and the second divided member are in the posture in which the capsule insertion hole is exposed so that the side wall restricts the advance movement of the capsule puncture needle.

* * * * *